United States Patent [19]

Hidaka et al.

[11] Patent Number: 4,678,783

[45] Date of Patent: Jul. 7, 1987

[54] SUBSTITUTED ISOQUINOLINESULFONYL COMPOUNDS

[75] Inventors: Hiroyoshi Hidaka, Tsu; Takanori Sone, Nobeoka, both of Japan

[73] Assignee: Asahi Kasei Kogyo Kabushiki Kaisha, Japan

[21] Appl. No.: 813,973

[22] Filed: Dec. 27, 1985

[30] Foreign Application Priority Data

Dec. 27, 1984 [JP] Japan .................. 59-273908
Apr. 2, 1985 [JP] Japan .................. 60-68512

[51] Int. Cl.⁴ .................. A61K 31/495; A61K 31/47; C07D 401/12; C07D 217/22
[52] U.S. Cl. .................. 514/218; 514/253; 514/307; 514/309; 540/470; 540/575; 544/363; 546/139; 546/141
[58] Field of Search ............ 546/141, 139; 544/363; 514/253, 307, 309, 218; 540/575, 470

[56] References Cited

U.S. PATENT DOCUMENTS 4,315,935  2/1982  Ali .................. 546/139
4,456,737  6/1984  Hidaka et al. .......... 544/363
4,525,589  6/1985  Hidaka et al. .......... 546/139

FOREIGN PATENT DOCUMENTS 0109023  5/1984  European Pat. Off.
59-93054 5/1984  Japan.

Primary Examiner—Glennon H. Hollrah
Assistant Examiner—James H. Turnipseed
Attorney, Agent, or Firm—Finnegan, Henderson, Farabow, Garrett & Dunner

[57] ABSTRACT

An isoquinolinesulfonyl compound represented by the formula (I):

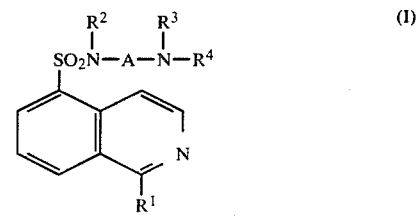

wherein
$R^1$ : H, Cl, OH
A : unsubstituted or substituted ethylene or alkylene
$R^2$, $R^3$: H, alkyl, jointly forming unsubstituted or substituted ethylene or trimethylene
$R^4$ : H, alkyl, amidino or an acid salt thereof.

They can be prepared, for example, by converting 1-$R^1$ substituted-5-isoquinolinesulfonic acid to the corresponding sulfonyl chloride and subsequently reacting the chloride with a compound of formula

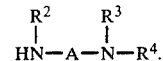

They can be advantageously utilized as vasodilator, cerebral circulation ameliorator, antihypertensive agent and drugs for prevention and treatment of various circulatory organ diseases.

19 Claims, No Drawings

SUBSTITUTED ISOQUINOLINESULFONYL COMPOUNDS

This invention relates to substituted isoquinolinesulfonyl compounds. More particularly, this invention is concerned with isoquinolinesulfonyl compounds which are a novel compound that affects the smooth muscle of a mammal, thereby being a valuable drug such as vasodilator, cerebral circulation ameliorator, antihypertensive agent and drugs for prevention and treatment of angina, cerebrovascular thrombosis, hypertonia, arteriosclerosis, cerebral apoplexy and other circulatory organ diseases.

Known in the art are compounds which are useful to treat circulatory organ diseases and which are represented by the following formulae:

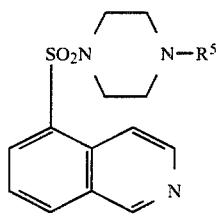

(disclosed in U.S. Pat. No. 4,525,589)

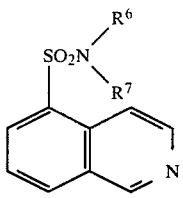

(disclosed in the above-mentioned patent)

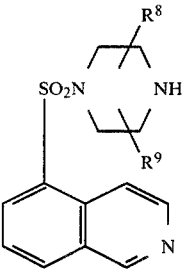

(disclosed in the above-mentioned patent)

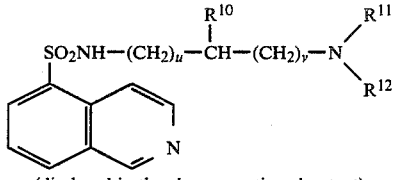

(disclosed in the above-mentioned patent)

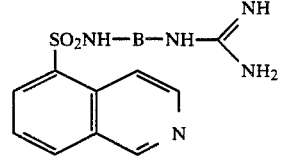

(disclosed in Japanese Patent Application Laid-Open Specification No. 59-93054/1984).

In the above formulae, $R^5$ represents an alkyl group, an aryl group, an aralkyl group, a benzoyl group, a cinnamyl group, a furoyl group or a group of the formula:

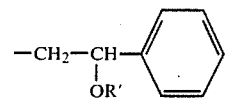

in which R' represents a low molecular alkyl group.

$R^6$ and $R^7$ each independently represent a hydrogen atom or a lower alkyl group, or $R^6$ and $R^7$ are bonded with each other directly or through the medium of an oxygen atom or a nitrogen atom to form a heterocyclic ring in cooperation with the adjacent nitrogen atom. $R^8$ represents a hydrogen atom or an alkyl group having 1 to 10 carbon atoms. $R^9$ represents a group selected from alkyl, aryl and aralkyl groups each having 1 to 10 carbon atoms. $R^{10}$ represents a hydrogen atom or a group selected from alkyl and aryl groups having 1 to 10 carbon atoms. $R^{11}$ and $R^{12}$ each independently represent a hydrogen atom or a group selected from alkyl, aryl and aralkyl groups each having 1 to 10 carbon atoms, or $R^{11}$ and $R^{12}$ are bonded with each other directly or through the medium of an oxygen atom to form a heterocyclic ring with an adjacent nitrogen atom. Symbols u and v each independently represent an integer of 0 to 9. B represents an alkylene group having n carbon atoms substituted with m groups selected from alkyl, aryl and aralkyl groups having 1 to 10 carbon atoms, in which n is a positive integer not greater than 10 and m is an integer of 0 to 2×n.

However, there is still a strong demand in the art for a more effective drug which can be advantageously utilized as vasodilator, cerebral circulation ameliorator, antihypertensive agent and drugs for prevention and treatment of angina, cerebrovascular thrombosis, hypertonia, arteriosclerosis, cerebral apoplexy and other circulatory organ diseases. This is especially so in the current aging society in which the number of aged people is increasing.

We have made extensive and intensive studies on various compounds, especially isoquinolinesulfonyl moiety-containing compounds, and their activities against such diseases. As a result, it has unexpectedly been found that novel, specifically substituted isoquinolinesulfonyl compounds are capable of increasing the diameter of a blood vessel and hence are useful to prevent and treat the above-mentioned diseases. Moreover, it has unexpectedly been found that they are useful to prevent and treat the delayed cerebral vasospasm occurring after the subarachnoid hemorrhage in humans. As far as the inventors' knowledge extends, there has not been any drug which can prevent or treat the delayed cerebral vasospasm occurring after the subarachnoid hemorrhage in humans. Based on these novel findings, we have completed this invention.

It is, therefore, an object of the present invention to provide a novel species of substituted isoquinolinesulfonyl compounds which are capable of increasing the diameter of a blood vessel and hence can be advantageously utilized as vasodilator, cerebral circulation ameliorator, antihypertensive agent and drugs for prevention and treatment of angina, cerebrovascular thrombosis, hypertonia, arteriosclerosis, cerebral apoplexy, the delayed cerebral vasospasm occurring after the subarachnoid hemorrhage in human, and other circulatory organ diseases.

The foregoing and other objects, features and advantages of the present invention will be apparent to those skilled in the art from the following detailed description and appended claims.

According to the present invention, there is provided an isoquinolinesulfonyl compound represented by the formula (I):

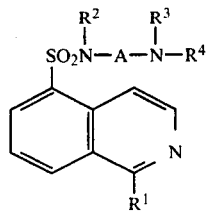

wherein $R^1$ represents a hydrogen atom, a chlorine atom or a hydroxyl group; and when $R^1$ represents a hydrogen atom, A represents an ethylene group unsubstituted or substituted with an alkyl group having 1 to 6 carbon atoms, a phenyl group or a benzyl group, $R^2$ and $R^3$ are directly bonded with each other, thereby forming a trimethylene group unsubstituted or substituted with an alkyl group having 1 to 6 carbon atoms, a phenyl group or a benzyl group, and $R^4$ represents a hydrogen atom or an alkyl group having 1 to 6 carbon atoms; and when $R^1$ represents a chlorine atom or a hydroxyl group, A represents an alkylene group having 2 to 6 carbon atoms, said group being unsubstituted or substituted with an alkyl group having 1 to 6 carbon atoms, $R^2$ and $R^3$ are not bonded with each other and each independently represent a hydrogen atom or an alkyl group having 1 to 6 carbon atoms, or $R^2$ and $R^3$ are directly bonded with each other, thereby forming an ethylene group unsubstituted or substituted with an alkyl group having 1 to 6 carbon atoms or a trimethylene group unsubstituted or substituted with an alkyl group having 1 to 6 carbon atoms, and $R^4$ represents a hydrogen atom, an alkyl group having 1 to 6 carbon atoms or an amidino group;

or an acid salt thereof.

With respect to the above-mentioned alkyl groups, they may be a straight chain group or a branched chain group.

Examples of the isoquinolinesulfonyl compound represented by the formula (I) according to the present invention are as follows:

(1) 1-(5-isoquinolinesulfonyl)homopiperazine
(2) 1-(5-isoquinolinesulfonyl)-2-methylhomopiperazine
(3) 1-(5-isoquinolinesulfonyl)-3-methylhomopiperazine
(4) 1-(5-isoquinolinesulfonyl)-6-methylhomopiperazine
(5) 1-(5-isoquinolinesulfonyl)-2,3-dimethylhomopiperazine
(6) 1-(5-isoquinolinesulfonyl)-3,3-dimethylhomopiperazine
(7) 1-(5-isoquinolinesulfonyl)-3-ethylhomopiperazine
(8) 1-(5-isoquinolinesulfonyl)-3-propylhomopiperazine
(9) 1-(5-isoquinolinesulfonyl)-3-isobutylhomopiperazine
(10) 1-(5-isoquinolinesulfonyl)-3-phenylhomopiperazine
(11) 1-(5-isoquinolinesulfonyl)-3-benzylhomopiperazine
(12) 1-(5-isoquinolinesulfonyl)-6-ethylhomopiperazine
(13) 1-(5-isoquinolinesulfonyl)-6-propylhomopiperazine
(14) 1-(5-isoquinolinesulfonyl)-6-butylhomopiperazine
(15) 1-(5-isoquinolinesulfonyl)-6-pentylhomopiperazine
(16) 1-(5-isoquinolinesulfonyl)-6-hexylhomopiperazine
(17) 1-(5-isoquinolinesulfonyl)-6-phenylhomopiperazine
(18) 1-(5-isoquinolinesulfonyl)-6-benzylhomopiperazine
(19) 1-(5-isoquinolinesulfonyl)-4-methylhomopiperazine
(20) 1-(5-isoquinolinesulfonyl)-4-ethylhomopiperazine
(21) 1-(5-isoquinolinesulfonyl)-4-propylhomopiperazine
(22) 1-(5-isoquinolinesulfonyl)-4-butylhomopiperazine
(23) 1-(5-isoquinolinesulfonyl)-4-hexylhomopiperazine
(24) N-(2-aminoethyl)-1-chloro-5-isoquinolinesulfonamide
(25) N-(4-aminobuthyl)-1-chloro-5-isoquinolinesulfonamide
(26) N-(2-amino-1-methylethyl)-1-chloro-5-isoquinolinesulfonamide
(27) N-(1-aminomethylpentyl)-1-chloro-5-isoquinolinesulfonamide
(28) N-(2-amino-3-methylbutyl)-1-chloro-5-isoquinolinesulfonamide
(29) N-(3-di-n-butylaminopropyl)-1-chloro-5-isoquinolinesulfonamide
(30) N-[2-(N-cyclohexyl-N-methylamino)ethyl]-1-chloro-5-isoquinolinesulfonamide
(31) N-(2-guanidinoethyl)-1-chloro-5-isoquinolinesulfonamide
(32) N-(4-guanidinobutyl)-1-chloro-5-isoquinolinesulfonamide
(33) N-(2-guanidino-1-methylethyl)-1-chloro-5-isoquinolinesulfonamide
(34) N-(1-guanidinomethylpentyl)-1-chloro-5-isoquinolinesulfonamide
(35) N-(2-guanidino-3-methylbutyl)-1-chloro-5-isoquinolinesulfonamide
(36) N-(3-guanidino-2-methylpropyl)-1-chloro-5-isoquinolinesulfonamide
(37) N-(4-guanidino-3-methylbutyl)-1-chloro-5-isoquinolinesulfonamide
(38) 1-(1-chloro-5-isoquinolinesulfonyl)-3-methylpiperazine
(39) 1-(1-chloro-5-isoquinolinesulfonyl)-3-ethylpiperazine
(40) 1-(1-chloro-5-isoquinolinesulfonyl)-3-isobutylpiperazine
(41) 1-(1-chloro-5-isoquinolinesulfonyl)-2,5-dimethylpiperazine
(42) 1-(1-chloro-5-isoquinolinesulfonyl)-4-methylpiperazine
(43) 1-(1-chloro-5-isoquinolinesulfonyl)-4-amidinopiperazine
(44) 1-(1-chloro-5-isoquinolinesulfonyl)-4-amidinohomopiperazine
(45) 1-(1-chloro-5-isoquinolinesulfonyl)-4-amidino-2-methylpiperazine
(46) 1-(1-chloro-5-isoquinolinesulfonyl)-4-amidino-2,5-dimethylpiperazine
(47) N-(2-aminoethyl)-1-hydroxy-5-isoquinolinesulfonamide
(48) N-(4-aminobutyl)-1-hydroxy-5-isoquinolinesulfonamide
(49) N-(2-amino-1-methylethyl)-1-hydroxy-5-isoquinolinesulfonamide
(50) N-(1-aminomethylpentyl)-1-hydroxyl-5-isoquinolinesulfonamide

(51) N-(2-amino-3-methylbutyl)-1-hydroxy-5-isoquinolinesulfonamide
(52) N-(3-di-n-butylaminopropyl)-1-hydroxy-5-isoquinolinesulfonamide
(53) N-[2-(N-cyclohexyl-N-methylamino)ethyl]-1-hydroxy-5-isoquinolinesulfonamide
(54) N-(2-guanidinoethyl)-1-hydroxy-5-isoquinolinesulfonamide
(55) N-(4-guanidinobutyl)-1-hydroxy-5-isoquinolinesulfonamide
(56) N-(2-guanidino-1-methylethyl)-1-hydroxy-5-isoquinolinesulfonamide
(57) N-(1-guanidinomethylpentyl)-1-hydroxy-5-isoquinolinesulfonamide
(58) N-(2-guanidino-3-methylbutyl)-1-hydroxy-5-isoquinolinesulfonamide
(59) N-(3-guanidino-2-methylpropyl)-1-hydroxy-5-isoquinolinesulfonamide
(60) N-(3-guanidino-3-methylbutyl)-1-hydroxy-5-isoquinolinesulfonamide
(61) 1-(1-hydroxy-5-isoquinolinesulfonyl)-3-methylpiperazine
(62) 1-(1-hydroxy-5-isoquinolinesulfonyl)-3-etylpiperazine
(63) 1-(1-hydroxy-5-isoquinolinesulfonyl)-3-isobutylpiperazine
(64) 1-(1-hydroxy-5-isoquinolinesulfonyl)-2,5-dimethylpiperazine
(65) 1-(1-hydroxy-5-isoquinolinesulfonyl)-4-methylpiperazine
(66) 1-(1-hydroxy-5-isoquinolinesulfonyl)-4-amidinopiperazine
(67) 1-(1-hydroxy-5-isoquinolinesulfonyl)-4-amidinohomopiperazine
(68) 1-(1-hydroxy-5-isoquinolinesulfonyl)-4-amidino-2-methylpiperazine
(69) 1-(1-hydroxy-5-isoquinolinesulfonyl)-4-amidino-2,5-dimethylpiperazine
(70) N-(2-methylaminoethyl)-1-chloro-5-isoquinolinesulfonamide
(71) N-(2-ethylaminoethyl)-1-chloro-5-isoquinolinesulfonamide
(72) N-(2-propylaminoethyl)-1-chloro-5-isoquinolinesulfonamide
(73) N-(2-butylaminoethyl)-1-chloro-5-isoquinolinesulfonamide
(74) N-(2-hexylaminoethyl)-1-chloro-5-isoquinolinesulfonamide
(75) 1-(1-chloro-5-isoquinolinesulfonyl)piperazine
(76) 1-(1-chloro-5-isoquinolinesulfonyl)homopiperazine
(77) N-(2-methylaminoethyl)-1-hydroxy-5-isoquinolinesulfonamide
(78) N-(2-ethylaminoethyl)-1-hydroxy-5-isoquinolinesulfonamide
(79) N-(2-propylaminoethyl)-1-hydroxy-5-isoquinolinesulfonamide
(80) N-(2-butylaminoethyl)-1-hydroxy-5-isoquinolinesulfonamide
(81) N-(2-hexylaminoethyl)-1-hydroxy-5-isoquinolinesulfonamide
(82) 1-(1-hydroxy-5-isoquinolinesulfonyl)piperazine
(83) 1-(1-hydroxy-5-isoquinolinesulfonyl)homopiperazine According to the present invention, there is further provided an acid salt of isoquinoline derivatives. The salt is an untoxic salt which is pharmacologically accepted. As examples of the acid, there may be mentioned such inorganic acids as hydrochloric acid, hydrobromic acid, phosphoric acid and sulfuric acid and such organic acids as acetic acid, citric acid, tartaric acid, lactic acid, succinic acid, fumaric acid, maleic acid and methanesulfonic acid.

The compound of formula (I) according to the present invention may be prepared, for example, by the following methods, (a) to (e).

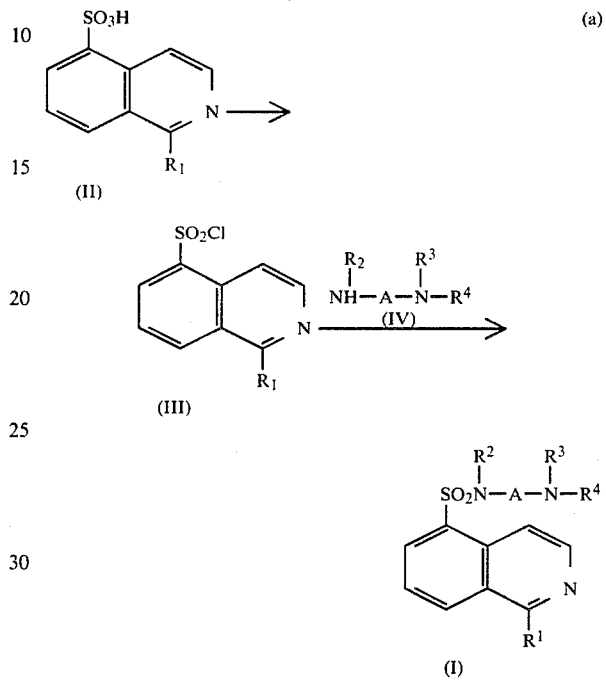

wherein $R^1$ represents a hydrogen atom or a chlorine atom, and A, $R^2$, $R^3$ and $R^4$ are as defined above.

Among the starting compounds represented by formula (II), a compound in which $R^1$ is a hydrogen atom is a known compound disclosed in prior art publications, but a compound in which $R^1$ is a chlorine atom, i.e., 1-chloro-5-isoquinolinesulfonic acid, is a new compound never disclosed in prior art publications, which is prepared as follows.

1-chloroisoquinoline is dropwise added to 2 to 20, preferably 3 to 10, equivalent of forming sulfuric acid while cooling with ice to carry out a reaction at 10° to 120° C., preferably at 20° to 100° C., for 4 to 24 hours. The reaction solution is poured on ice water to obtain a crystal of 1-chloro-5-isoquinolinesulfonic acid.

The conversion from the compound of formula (II) to sulfonyl chloride may be carried out by such known methods as a method where thionyl chloride is reacted with the compound of formula (II) in the presence of N,N-dimethylfolmamide and a method where phosphorous pentachoride is reacted with the compound of formula (II).

As the compound of formula (IV) to be used in this reaction, there may be mentioned homopiperazine, 2-methylhomopiperazine, 2-ethylhomopiperazine, 2-propylhomopiperazine, 2-butylhomopiperazine, 2-isobutylhomopiperazine, 2-phenylhomopiperazine, 2-benzylhomopiperazine, 1-methylhomopiperazine, 1-ethylhomopiperazine, 1-propylhomopiperazine, 1-butylhomopiperazine, 1-iso-butylhomopiperazine, 1-hexylhomopiperazine, 1-phenylhomopiperazine, 1-benzylhomopiperazine, 6-methylhomopiperazine, 6-ethylhomopiperazine, 6-propylhomopiperazine, 6-butylhomopiperazine, 6-hexylhomopiperazine, 6-benzylhomopiperazine, 2,3-dimethylhomopiperazine, 2,2-dimethyl-homopiperazine, 4-methylhomopiperazine, 4-ethylhomopiperazine, 4-propylhomopiperazine, 4-butylhomopiperazine, 4-pentylhomopiperazine, 2-hexylhomopiperazine, piperazine, 1methylpiperazine, 2-methylpiperazine, 2-ethylpiperazine, 2-propylpiperazine, 2-butylpiperazine, 2-isobutylpiperazine, 2,3-dimethylpiperazine, 2,5-dimethylpiperazine, ethylenediamine, 1,2-diaminoethane, 1,4-diaminobutane, 3,3-di-n-butylaminopropylamine, 1-amidino-3-methylpiperazine, 3-guanidino-2-methylpropylamine, 4-guanidino-3-methylbutylamine, 1-amidinopiperazine, 1-amidinohomopiperazine, 1-amidino-2,5-dimethylpiperazine, etc.

The reaction between the compound of formula (III) and the compound of formula (IV) can be carried out in the presence or absence of an acid acceptor. Exemplary acid acceptors which can be employed include alkali metal compounds such as sodium bicarbonate, sodium hydroxide, sodium carbonate, sodium hydride, potassium carbonate, potassium hydroxide and sodium alkoxide such as sodium methoxide and sodium ethoxide; and organic tertiary amines such as pyridine, triethylamine and triethylenediamine. In general, this reaction is carried out in the presence of a reaction medium. Exemplary reaction media which can be employed include halogenated hydrocarbon such as chloroform, dichloromethane; alcohols such as methanol, ethanol and butanol; ethers such as tetrahydrofuran and dioxane; N,N-dimethylformamide; dimethyl sulfoxide; acetonitrile; and water. The reaction media may be used singly or in combination with one another.

The amount of the compound of formula (IV) which can be employed is at least 1 mol and typically ranges from 1 to 20 mols, preferably from 1 to 10 mols per mol of the compound of formula (III). A more preferred amount of the compound of formula (IV) ranges from 1 to 3 mols per mol of the compound of formula (III) when the acid acceptor is present, and from 2.5 to 5 mols per mol of the compound of formula (III) when the acid acceptor is absent.

The amount of the acid acceptor employed is preferably about 0.5 to about 10 equivalents and more preferably about 1 to 6 equivalents for each mol of the compound of formula (IV). The reaction between the compound of formula (III) and the compound of formula (IV) can be carried out typically at a temperature of from about −30° C. to 120° C. and preferably from about −20° C. to 50° C.

The reaction time which can be employed is typically about 0.5 to 48 hours and preferably about 0.5 to 6 hours.

(b) The compound of formula (V):

wherein $R^2$, $R^3$ and A are as defined above, and X represents a protective group, is reacted with the compound of formula (III) to obtain the intermediate of formula (VI):

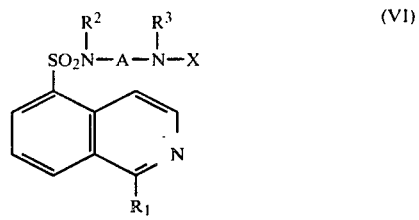

wherein $R^2$, $R^3$, A and X are as defined above, and $R^1$ represents a hydrogen atom or a chlorine atom. The protective group of said intermediate is eliminated by a customary method to prepare the compound of formula (VII):

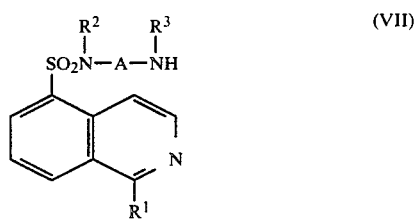

wherein $R^1$ represents a hydrogen atom or a chlorine atom, and $R^2$, $R^3$ and A are as defined above.

As the protective group X, there may be mentioned formyl group, acetyl group, benzoyl group, benzyloxycarbonyl group, t-butoxycarbonyl group, etc.

When the compound of formula (VI) is prepared, it is preferable to use an acid acceptor. As the acid acceptor, there may be used alkali metal compounds such as sodium hydrogenencarbonate, sodium carbonate, potassium carbonate and sodium hydroxide, and organic tertiary amines such as pyridine, trimethylamine, triethylamine. The amount of the acid acceptor to be used is preferably from 1 to 3 moles per mol of the compound of formula (III).

The amount of the compound of formula (V) to be used is preferably from 1 to 2 moles per mol of the compound of formula (III). Further, the reaction medium, the reaction temperature and the reaction time are preferably the same as those of (a).

The protective group X may be eliminated from the compound of formula (VI) by various methods, all of which are known and customary methods. The method to be employed depends on the protective group X. That is, in the case of formyl group, acetyl group or benzoyl group, hydrolysis by an acid or a base may be employed; in the case of t-butoxycarbonyl group, hydrolysis by an acid may be employed; and in the case of benzyloxycarbonyl group, hydrolysis by an acid or reductive cleavage by the addition of hydrogen may be employed.

(c) A compound represented by the formula (VII) in which $R^1$ represents a chlorine atom is reacted with a compound represented by the formula (VIII):

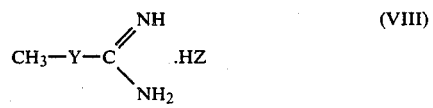

wherein Y represents an oxygen atom or a sulfur atom and HZ an acid residue, to obtain a compound represented by the formula (IX):

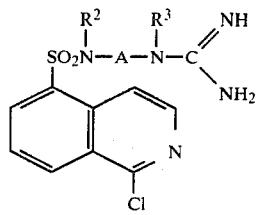 (IX)

wherein $R^2$, $R^3$ and A are as defined above.

As examples of the compound represented by the formula (VIII), there may be mentioned S-methylisothiourea sulfate, O-methylisourea hydrochloride, O-methylisourea sulfate and the like.

The reaction may be generally effected in the presence of a reaction medium. As examples of the reaction medium which may be preferably employed, there may be mentioned water or a mixture of water with an alkanol such as methanol or ethanol, acetonitrile or acetone.

It is preferred that the compound represented by the formula (VIII) be used in an amount of 1.5 to 4 times, by mole, the amount of the compound represented by the formula (VII).

The reaction is preferably effected in an alkaline solution having a pH value of 9 or higher at 50 to 100° C. for 1 to 4 hours.

(d) 1-chloro-5-isoquinolinesulfonyl chloride is reacted with a compound represented by the formula (X):

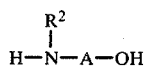 (X)

wherein $R^2$ and A are as defined above, to obtain a compound represented by the formula (XI):

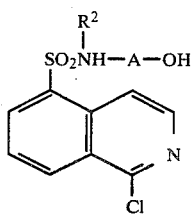 (XI)

wherein $R^2$ and A are as defined above. The thus obtained compound represented by the formula (XI) is then reacted with p-toluenesulfonyl chloride to obtain a compound represented by the formula (XII):

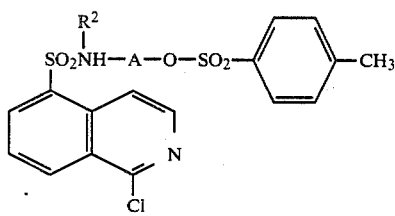 (XII)

wherein $R^2$ and A are as defined above. Subsequently, the thus obtained compound represented by the formula (XII) is reacted with an amine represented by the formula (XIII):

 (XIII)

wherein $R^3$ is as defined above and $R^{13}$ represents an alkyl group having 1 to 4 carbon atoms or a hydrogen atom, to obtain a compound represented by the formula (XIV):

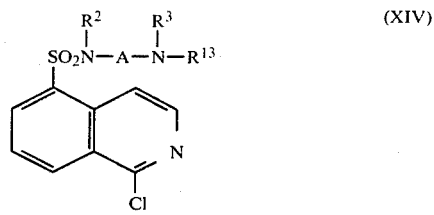 (XIV)

wherein $R^2$, $R^3$, $R^{13}$ and A are as defined above.

The reaction of 1-chloro-5-isoquinolinesulfonyl chloride with the compound represented by the formula (X) may be effected in substantially the same manner as described in the above method (b) with respect to the reaction of the compound represented by the formula (III) with the compound represented by the formula (V).

The reaction of the compound represented by the formula (XI) with p-toluenesulfonyl chloride to obtain the compound represented by the formula (XII) may be effected according to a method described in L. F. Fieser and M. Fieser, "Reagents for Organic Synthesis", vol I, 1180 (1967).

The reaction of the compound represented by the formula (XII) with the amine represented by the formula (XIII) may be effected in a reaction medium, e.g. an alkanol such as methanol or ethanol, a halogenated hydrocarbon such as methylene chloride, chloroform, or an ether such as diethyl ether, dioxane or tetrahydrofuran. The reaction temperature is preferably 10° C. to 70° C. The reaction time is generally 30 min to one day.

(e) A compound represented by the formula (XVI) is obtained by treating a compound represented by the formula (XV) which has been prepared by the above-mentioned method (a), (b), (c) or (d) with an inorganic acid.

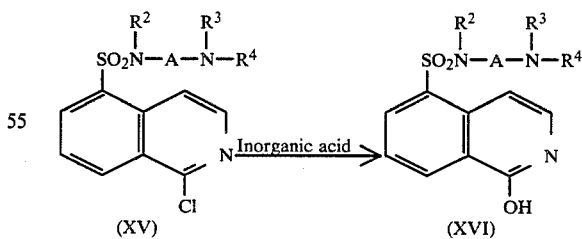

wherein $R^2$, $R^3$, $R^4$ and A are as defined above.

As examples of the inorganic acid, there may be mentioned hydrochloric acid, sulfuric acid and nitric acid. The concentration of the inorganic acid is preferably 0.25 mol/liter to 10 mols/liter. The reaction is preferably effected at 50° C. to 100° C. for 2 to 6 hours.

The isoquinolinesulfonyl compound represented by the formula (I) and salt thereof with a pharmacologically acceptable acid according to the present invention can increase the diameter of a blood vessel, and have an excellent smooth muscle relaxation action for a blood vessel, an excellent flow volume increase action for blood and an antihypertensive action. Hence, they can be advantageously utilized as vasodilator, cerebral circulation ameliorator, antihypertensive agent and drugs for prevention and treatment of angina, cerebrovascular thrombosis, hypertonia, arteriosclerosis, cerebral apoplexy, the delayed cerebral vasospasm occurring after the subarachnoid hemorrhage in humans, and the other circulatory organ diseases. The above-mentioned relaxation action for a blood vessel was confirmed by the relaxation of the mesenteric artery of a rabbit in accordance with the method described later. The above-mentioned flow volume increase action for blood was confirmed by the blood flow volume increase of dog's femoral and vertebral arteries in accordance with the method described later. The above-mentioned antihypertensive action was confirmed by the indirect tail plethysmographic method of systolic blood pressure after oral administration of test drugs using male spontaneously hypertensive rats in accordance with the method described later. The effects of the isoquinolinesulfonyl derivatives of this invention on a "two-hemorrhage" canine model of delayed cerebral vasospasm were examined. The method of inducing a cerebral vasospasm was the same as that reported by Varsos et al. (Journal of Neurosurgery, volume 58, p11–17, 1983). The intravenous administration of isoquinolinesulfonyl derivatives of this invention significantly reversed the experimental cerebral vasospasm. As far as is known, these isoquinolinesulfonyl derivatives are the first drugs which can reverse "two-hemorrhage" cerebral vasospasm by its systemic use. The present findings demonstrate that the isoquinolinesulfonyl derivatives of this invention will prevent or reverse the cerebral vasospasm occurring after the subarachnoid hemorrhage in humans.

Acute toxicity of the compounds of the present invention was determined according to the method given below, and the results are shown in Table 15. For example, 1-(5-isoquinolinesulfonyl)homopiperazine and 1-(1-hydroxy-5-isoquinolinesulfonyl)homopiperazine exhibited $LD_{50}$ values of 73.5 mg/kg and 145 mg/kg, respectively. It is known from the results that the acute toxicity of the compounds of the present invention is satisfactorily low.

Particularly, with respect to the relaxation action for a blood vessel, the compounds of the present invention have a high relaxation effect on smooth muscles. The effect will be demonstrated in Application Example 1 given hereinafter, using a spiral sample prepared from a mesenteric artery of a rabbit. For example, 1-(5-isoquinolinesulfonyl)homopiperazine according to the present invention has a $ED_{50}$ value, which indicates a concentration of the compound at which 50% relaxation is attained, of as low as 0.8 $\mu M$. This shows an excellent relaxation effect of the present compound on smooth muscles of blood vessels.

Further, with respect to the increase effect on blood flow, the compounds of the present invention were intravenously administered to dogs, and change in blood flow was measured plethysmographically in Application Example 3. At a dosage of 0.3 mg/kg, 1-(5isoquinolinesulfonyl)homopiperazine elicited 48% and 160% augmentation in the blood flows through femoral and vertebral arteries, respectively; and 1-(1-hydroxy-5-isoquinolinesulfonyl)-homopiperazine elicited 30% and 48% augmentation in the blood flows through femoral and vertebral arteries, respectively. As is apparent from the results the compounds of the present invention have a high increase effect on blood flow.

The present invention, in still a further aspect, is directed to pharmaceutical compositions incorporating a compound of the formula (I) hereof as an essential active component in admixture with a pharmaceutically acceptable non-toxic carrier.

The compound of the present invention may be administered to humans orally or by intravenous injection. The compound may be orally administered in an amount of 20 to 300 mg per day for an adult in 2 to 3 administrations, and for a period of from 1 week to 2 months daily. Both the daily dosage and the period of administration vary to some extent depending on the condition of the patient. Further, the compound of the present invention may preferably be administered intravenously for the prevention and treatment of the cerebral vasospasm occurring after the subarachnoid hemorrhage in humans, the treatment of the cerebral embolism in the acute stadium, etc. The compound may be dissolved in physiological salt solution and then administered in an amount of 10 to 100 mg per day for an adult over a period of 1 to 24 hours. The dosage and the administration time vary to some extent depending on the condition of the patient.

Still further, the compound of the present invention may be used in combination with other drugs for the treatment of respiratory diseases. Depending on the condition of the patient, the compound of the present invention may be used in combination with, for example, a diuretic, an antihypertensive agent, a $\beta$-blocker, a cerebral metabolism ameliorator, etc.

Effect of the compounds of the present invention were examined in the following Application examples according to the methods given below.

1. Relaxation of Mesenteric Artery

A rabbit of Japanese local variety weighing about 3 kg was subjected to blood-letting to death. Then, abdomen of the rabbit was dissected to pick up a mesenteric artery. According to the customary method, the artery was cut into a spiral having a width of 2 mm and a length of 25 mm, and suspended in a 20-ml organ bath filled with Krebs-Henseleit nutrient solution through which a mixture gas consisting of 95% by volume of $O_2$ and 5% by volume of $CO_2$ had been bubbled. The free end of the suspended artery was connected to an isometric transducer (FD Pickup TB-912T, trade name of NIHON KODEN CO., LTD.) and tensed at a load of 15 g. Thus, the shrinkage and relaxation of the artery was ready to be measured as a load on the transducer. To the organ bath, KCl was added in an amount which makes the artery shrink at a half length that in 15 to 20 mM aqueous solution. Then, hydrochlorides of the compounds of the present invention were added to the organ bath to observe relaxation effect on the artery. Measurement was made of concentrations of the hydrochloride ($ED_{50}$) which attained 50% of the complete relaxation.

2. Reduction of Blood Pressure

Male spontaneously hypertensive rats (SHR, Wister Kyoto) weighing 300 to 350 g were used. Systolic blood pressure was measured indirectly by the tail plethysmographic method in conscious SHR, just prior to, and 1, 2, 4 and 6 hours after oral administration of test drugs. Test drugs, dissolved in deionized water, were administered orally in a volume of 10 ml-solution/kg-rat. Reduction in systolic blood pressure (ΔP, mmHg) was calculated by substracting a systolic blood pressure after administration from that just prior to administration.

3. Blood Flow Volume Increase of Femoral and Vertebral Arteries

Mongrel dogs weighing 8 to 15 kg were put under anesthesia by intravenously administering pentobarbital in a dose of 35 mg/kg. A plethysmographic probe (manufactured and sold by NIHON KODEN CO., LTD.) was mounted on the femoral and vertebral arteries, and blood flow volume was measured by means of a electromagnetic blood flowmeter (type:MF-27, manufactured and sold by NIHON KODEN CO., LTD.). Under these conditions, compounds of the present invention were intravenously administered through a polyethylene tube inserted to a femoral veinlet, and change in blood flow volume was measured by means of the electromagnetic blood flowmeter.

4. Effect on a "Two-Hemorrhage" Canine Model of Delayed Cerebral Vasospasm

Mongrel dogs of either sex weighing 7 to 11 kg were used. All procedures were performed under anesthesia with sodium pentobarbital (20 to 30 mg/kg, intravenous administration) after premedication with ketamine hydrochloride (12 mg/kg, intramuscular administration) and spontaneous respiration through an endotracheal intubation.

The method of inducing a "two-hemorrhage" canine model of subarachnoid hemorrhage was essentially the same as that reported by Varsos et al. (Journal of Neurosurgery, volume 58, p 11–17, 1983); two successive administrations were effected, two days apart (on Day 1 and Day 3), of fresh autogenous blood into the cisterna magna. A control angiogram was taken by a direct puncture of the vertebral artery on Day 1 before the blood injection. The second angiogram was made to confirm the presence of a vasospasm on Day 7.

On Day 7, after the occurrence of a chronic vasospasm was confirmed by the second angiogram, the compounds of the present invention were intrvenously infused from the femoral vein with a Harvard pump over a period of 30 minutes. Angiograms were taken from the initiation of the infusion.

The diameter of the basilar artery was measured on the angiogram by means of a microdensitometer (SAKURA DENSITOMETER PD-7R). The effect on this cerebral vasospasm model of the compounds of the present invention was expressed as an increased percentage of the diameter after the infusion of the compounds of the present invention to that before the infusion.

5 Acute Toxicity

Using ddY male mice, acute toxicity of the compounds of the present invention was examined according to the method proposed by K. Takagi et al. (K. Takagi and H. Ozawa, "Experimental Techniques in Pharmacology," p200-206 (1960), NANZANDO CO., LTD.).

REFERENCE EXAMPLE

To 1200 ml of thionyl chloride were added 150 g of 5-isoquinolinesulfonic acid and 0.4 ml of N,Ndimethylformamide. Then, the resulting mixture was refluxed while heating at 80° to 85 ° C for 3 hours, followed by removal of the thionyl chloride under reduced pressure. Subsequently, 300 ml of dichloromethane was added to the reaction mixture to precipitate crystals. The precipitated crystals were separated by filtration, washed with 100 ml of dichloromethane, and then dried under reduced pressure to obtain 170 g of 5-isoquinolinesulfonyl chloride hydrochloride.

EXAMPLE 1

145 g of 1-Chloroisoquinoline was dropwise added to 500 g of 60% fuming sulfuric acid while cooling with ice. Then, the temperature was elevated to 80° C. and the reaction was effected while stirring for 18 hours. The obtained reaction mixture was added to 1 kg of ice water, followed by stirring for 2 hours at 5° C. to precipitate crystals. The thus obtained crystals were separated by filtration, washed with 100 ml of methanol and then with 100 ml of ether, and dried under reduced pressure to obtain 126 g of 1-chloro-5-isoquinolinesulfonic acid. The compound was analyzed to give the following data.

Melting Point : >250° C.
IR absorption spectrum $(cm^{-1})$: 1640,1600,1330,1150.
NMR spectrum ($D_2O$) : 7.6–7.9(1H), 8.0–8.7(4H).

EXAMPLE 2

To 40 ml of thionyl chloride were added 2.93 g of 1-chloro-5-isoquinolinesulfonic acid as obtained in Example 1 and 0.4 ml of N,N-dimethylformamide. Then, the resulting mixture was refluxed while heating at 80° to 85° C. for 2 hours, followed by removal of the thionyl chloride under reduced pressure. Subsequently, 10 ml of dichloromethane was added to the reaction mixture to precipitate crystals, followed by separation of the crystals by filtration. The crystals thus obtained were washed with 10 ml of dichloromethane, and then dried under reduced pressure to obtain 3.06 g of 1-chloro-5-isoquinolinesulfonyl chloride hydrochloride. The compound was analyzed to give the following data.

IR absorption spectrum $(cm^{-1})$: 1610,1500,1320,1160.
NMR spectrum ($D_2O$) : 7.6–7.9(1H), 8.0–8.7(4H).
Mass spectrum (m/e) : 261, 263

EXAMPLE 3

In 50 ml of ice water was dissolved 5.5 g of 5-isoquinolinesulfonyl chloride hydrochloride as obtained in Reference Example, and the pH of the solution was adjusted to 6 with an aqueous sodium hydrogencarbonate saturated solution, followed by extraction with 100 ml of dichloromethane. The dichloromethane layer was added dropwise to a 50 ml of dichloromethane solution containing 5.0 g of homopiperazine for 20 minutes while cooling with ice. The mixture was stirred at a temperature of 15° C. to 20° C. for 2 hours, washed with water, and dried with anhydrous magnesium sulfate. Then, the dichloromethane was removed under reduced pressure to obtain an oily residue. The thus obtained oily residue was subjected to purification by the silica gel column chromatography (Wacogel C-200, 200 g; solvent: chloroform), thereby to obtain 5.1 g of 1-(5-isoquinolinesulfonyl)homopiperazine, i.e., compound (1), in a 88% yield. Compound (1) was analyzed to give the following data.

IR absorption spectrum (cm$^{-1}$): 3320,1620,1330,1150.

NMR spectrum (CDCl$_3$-DCl) : 2.1–2.7(2H), 3.6–4.2(8H), 7.6–7.9(1H), 8.1–8.8(4H), 9.3(1H).

Substantially the same procedures as described above were repeated except that each of the compounds of the formula (IV) as set forth in Table 1-1 was used in place of homopiperazine used above and that other reaction conditions were changed as indicated in Table 1-1. As a result, there were obtained 1-(5-isoquino- linesulfonyl)-3-methylhomopiperazine,i.e.,Compound (3); 1-(5-isoquinolinesulfonyl)-6-methylhomopiperazine,i.e.,-Compound (4); 1-(5-isoquinolinesulfonyl)-2,3-dimethyl-homopiperazine,i.e.,Compound (5); 1-(5-isoquinolinesulfonyl)-3,3-dimethylhomopiperazine, i.e.,Compound (6);1-(5-isoquinolinesulfonyl)-3-ethyl-homopiperazine,i.e.,Compound (7); 1-(5-isoquinoline-sulfonyl)-3-isobutylhomopiperazine,i.e.,Compound (9); 1-(5-isoquinolinesulfonyl)-3-phenylhomopiperazine, i.e.,Compound (10); 1-(5-isoquinolinesulfonyl)-6-ethyl-homopiperazine, i.e., Compound (12); 1-(5-isoquinolinesulfonyl)-6-propylhomopiperazine, i.e., Compound (13); 1-(5-isoquinolinesulfonyl)-6-hexyl-homopiperazine,i.e., Compound (16); 1-(5-isoquinolinesulfonyl)-6-benzylhomopiperazine,i.e., Compound (18). The yields and analytical values of these compounds are shown in Table 1-2.

duced pressure to obtain an oily residue. To the thus obtained oily residue was added 30 ml of a 25% hydrobromic acid solution in acetic acid, and the mixture was stirred for 5 hours at a temperature of 15° C. to 20° C. and then poured into 100 ml of ice water.

TABLE 1-1

| Run No. | 5-Isoquinoline-sulfonyl chloride hydrochloride(g) | Compound (IV) | (g) | Reaction temperature (°C.) | Reaction time (hr) |
|---|---|---|---|---|---|
| 3-1 | 2.77 | 2-methylhomo-piperazine | 3.42 | 10–15 | 2 |
| 3-2 | 2.77 | 6-methylhomo-piperazine | 3.42 | 10–15 | 2 |
| 3-3 | 2.77 | 2,3-dimethyl-homopiperazine | 3.84 | 10–15 | 2 |
| 3-4 | 2.77 | 2,2-dimethyl-homopiperazine | 3.84 | 10–15 | 10 |
| 3-5 | 2.77 | 2-ethylhomo-piperazine | 3.84 | 10–15 | 10 |
| 3-6 | 2.77 | 2-isobutylhomo-piperazine | 3.12 | 15–20 | 10 |
| 3-7 | 2.77 | 2-phenylhomo-piperazine | 3.52 | 15–20 | 15 |
| 3-8 | 1.38 | 6-ethylhomo-piperazine | 3.84 | 15–20 | 15 |
| 3-9 | 1.38 | 6-propylhomo-piperazine | 4.26 | 10–20 | 15 |
| 3-10 | 1.38 | 6-hexylhomo-piperazine | 5.52 | 10–20 | 15 |
| 3-11 | 1.38 | 6-benzylhomo-piperazine | 5.70 | 10–20 | 15 |

TABLE 1-2

| Run No. | Obtained Compound | Yield | Mass spectrum (m/e) | IR absorption spectrum (cm$^{-1}$) | NMR spectrum (CD$_3$OD-DCl) |
|---|---|---|---|---|---|
| 3-1 | (3) | 2.49 g (79%) | 305 | 3330, 1620 1340, 1160 | 1.0–1.2(3H), 2.0–2.7(2H), 3.6–4.2(7H), 7.6–7.9(1H), 8.1–8.3(4H), 9.3(1H) |
| 3-2 | (4) | 2.55 g (81%) | 305 | 3320, 1620 1330, 1150 | 0.8–1.0(3H), 2.0–2.8(1H), 3.6–4.2(8H), 7.6–7.9(1H), 8.1–8.8(4H), 9.3(1H) |
| 3-3 | (5) | 2.39 g (75%) | 319 | 3320, 1620 1320, 1160 | 0.9–1.2(6H), 2.1–2.7(2H), 3.6–4.2(6H), 7.6–7.9(1H), 8.1–8.8(4H), 9.3(1H) |
| 3-4 | (6) | 2.46 g (77%) | 319 | 3330, 1620 1330, 1150 | 1.0–1.1(6H), 2.1–2.8(2H), 3.6–4.2(6H), 7.6–7.9(1H), 8.1–8.8(4H), 9.3(1H) |
| 3-5 | (7) | 2.74 g (86%) | 319 | 3330, 1620 1330, 1150 | 0.8–1.1(3H), 1.9–2.8(4H), 3.5–4.2(7H), 7.6–7.9(1H), 8.1–8.8(4H), 9.3(1H) |
| 3-6 | (9) | 2.91 g (84%) | 347 | 3340, 1620 1330, 1150 | 0.9–1.0(6H), 1.4–2.8(5H), 3.6–4.2(7H), 7.6–7.9(1H), 8.1–8.8(4H), 9.3(1H) |
| 3-7 | (10) | 2.90 g (79%) | 367 | 3350, 1630 1340, 1160 | 2.1–2.7(2H), 3.6–4.2(7H), 7.1–7.9(6H), 8.1–8.8(4H), 9.3(1H) |
| 3-8 | (12) | 1.29 g (81%) | 319 | 3320, 1620 1330, 1150 | 0.8–1.0(3H), 1.1–1.8(2H), 2.2–2.8(1H), 3.6–4.2 (8H), 7.6–7.9(1H), 8.1–8.8(4H), 9.3(1H) |
| 3-9 | (13) | 1.47 g (88%) | 333 | 3330, 1620 1330, 1150 | 0.8–2.9(7H), 3.6–4.2(8H), 7.6–7.9(1H), 8.1–8.8(4H), 9.3(1H) |
| 3-10 | (16) | 1.28 g (68%) | 375 | 3330, 1620 1340, 1150 | 0.8–2.0(13H), 2.2–2.9(1H), 3.6–4.2(8H), 7.6–7.9(1H), 8.1–8.8(4H), 9.3(1H) |
| 3-11 | (18) | 1.47 g (77%) | 382 | 3330, 1620 1340, 1140 | 2.1–2.8(3H), 3.6–4.2(8H), 7.2(5H), 7.6–7.9(1H), 8.1–8.8(4H), 9.3(1H) |

EXAMPLE 4

In 50 ml of ice water was dissolved 5.5 g of 5-isoquinolinesulfonyl chloride hydrochloride as obtained in Reference Example, and the pH of the solution was adjusted to 6 with an aqueous sodium hydrogencarbonate saturated solution, followed by extraction with 100 ml of dichloromethane. The dichloromethane layer was added dropwise to a 50 ml of dichloromethane solution containing 6.0 g of 1-benzyloxycarbonyl-3-methyl-homopiperazine and 3.5 g of triethylamine for 1 hour while cooling with ice. The mixture was stirred at a temperature of 5° C. to 15° C. for 12 hours, washed with water, and dried with anhydrous magnesium sulfate. Then, the dichloromethane was removed under re- The pH of the aqueous layer was adjusted to 10 with a 5N aqueous sodium hydroxide solution, followed by extraction with chloroform. The chloroform layer was washed with water and dried with anhydrous magnesium sulfate. Then the chloroform was distilled off under reduced pressure to obtain an oily residue. The oily residue thus obtained was subjected to purification by the silica gen column chromatography (Wacogel C-200, 200 g; solvent: a 3% methanol solution in chloroform), thereby to obtain 3.38 g of 1-(5-isoquinolinesulfonyl)-2-methylhomopiperazine, i.e., Compound (2), in a 58% yield. Analytical data on Compound (2) are given below.

Mass spectrum (m/e): 305

IR absorption spectrum (cm$^{-1}$): 3320,1620,1330,1150.

NMR spectrum (CDCl$_3$-DCl): 1.0–1.2(3H), 2.0–2.8(2H), 3.6–4.2(7H), 7.6–7.9(1H), 8.1–8.8(4H), 9.3(1H).

EXAMPLE 5

In 10 ml of ice water was dissolved 1.38 g of 5-isoquinolinesulfonyl chloride hydrochloride as obtained in Reference Example. Then, the pH of the solution was adjusted to 6 with an aqueous sodium hydrogencarbonate solution, followed by extraction with 30 ml of dichloromethane. The dichloromethane layer was added dropwise to a 20 ml of dichloromethane solution containing 0.85 g of 1-methylhomopiperazine and 1.0 g of triethylamine while cooling with ice. The mixture was stirred at a temperature of 10° C. to 20° C. for 2 hours, washed with water, and dried with anhydrous magnesium sulfate. Then, the dichloromethane was removed under reduced pressure to obtain an oily residue. The thus obtained oily residue was subjected to purification by the silica gel column chromatography (Wacogel C-200, 80 g; solvent: a 3% methanol solution in chloroform), thereby to obtain 1.25 g of 1-(5-isoquinolinesulfonyl)-4-methylhomopiperazine, i.e., Compound (19), in a 86% yield. Analytical data on Compound (19) are given below.

Mass spectrum (m/e): 305

IR absorption spectrum (cm$^{-1}$): 1630,1340,1140.

NMR spectrum (CDCl$_3$-DCl): 2.0–2.8(5H), 3.6–4.2(8H), 7.6–7.9(1H), 8.1–8.8(4H), 9.3(1H).

Substantially the same procedures as described above were repeated except that each of the compounds of the formula (IV) as set forth in Table 2-1 was used in place of 1-methylhomopiperazine used above and that other reaction conditions were changed as indicated in Table 2-1. As a result, there were obtained 1-(5-isoquinolinesulfonyl)-4-ethylhomopiperazine,i.e., Compound (20); 1-(5-isoquinolinesulfonyl)-4-butylhomopiperazine,i.e.,Compound (22); 1-(5-isoquinolinesulfonyl)-4-hexylhomopiperazine, i.e.,Compound (23). The yields and analytical values of these compounds are shown in Table 2-2.

EXAMPLE 6

5 g of 1-(5-isoquinolinesulfonyl)homopiperazine (Compound(1)) as prepared in substantially the same manner as in Example 3 was dissolved in 40 ml of methanol, and the pH of the solution was adjusted to 6 with 1N hydrochloric acid. Then the solution was condensed under reduced pressure to obtain a crystalline residue. The crystalline residue thus obtained was recrystallized from methanol-ether to obtain 1-(5isoquinolinesulfonyl)homopiperazine hydrochloride. Analytical data on this compound are given below.

Melting point: 213°–215° C.

Elemental analysis (%):

(Calculated) C: 51.29, H: 5.53, N: 12.8. (Found) C: 51.50, H: 5.88, N: 12.90.

TABLE 2-1

| Run No. | 5-Isoquinolinesulfonyl chloride hydrochloride (g) | Compound (IV) | (g) | Triethylamine (g) | Reaction temperature (°C.) | Reaction time (hr) |
| --- | --- | --- | --- | --- | --- | --- |
| 5-1 | 1.0 (g) | 1-ethylhomopiperazine | 0.70 | 0.73 | 10–20 | 3 |
| 5-2 | 1.0 | 1-butylhomopiperazine | 0.85 | 0.73 | 10–20 | 3 |
| 5-3 | 1.0 | 1-hexylhomopiperazine | 1.0 | 0.73 | 10–20 | 3 |

TABLE 2-2

| Run No. | Obtained Compound | Yield | Mass spectrum (m/e) | IR absorption spectrum (cm$^{-1}$) | NMR spectrum (CD$_3$OD-DCl) |
| --- | --- | --- | --- | --- | --- |
| 5-1 | (20) | 1.02 g (84%) | 319 | 1630 1350 1150 | 0.9–1.2(3H), 2.1–2.8 (2H), 3.4–4.2(10H), 7.6–7.9(1H), 8.1–8.8 (4H), 9.3(1H) |
| 5-2 | (22) | 1.04 g (79%) | 347 | 1620 1330 1150 | 0.8–1.0(3H), 1.0–4.2 (16H), 7.6–7.9(1H), 8.1–8.8(4H), 9.3(1H) |
| 5-3 | (23) | 1.1 g (77%) | 375 | 1620 1330 1150 | 0.8–1.0(3H), 1.0–2.2 (10H), 3.0–4.2(10H), 7.6–7.9(1H), 8.1–8.8 (4H), 9.3(1H) |

Substantially the same procedures were repeated except that the starting compounds as indicated in Table 3 were used in place of Compound (1) used above, thereby to obtain hydrochlorides of respective starting compounds.

Elemental analysis data on the thus obtaining hydrochlorides are shown in Table 3.

EXAMPLE 7

To 40 ml of thionyl chloride were added 2.93 g of 1-chloro-5-isoquinolinesulfonic acid as obtained in Example 1 and 0.4 ml of N,N-dimethylformamide. Then, the resulting mixture was refluxed while heating at 80° to 85° C. for 2 hours, followed by removal of the thionyl chloride under reduced pressure to obtain a crystalline residue. The crystalline residue thus obtained was dissolved in a liquid consisting of 50 ml of water and 50 ml of dichloromethane, and the pH of the water layer was adjusted to 6.0 with an aqueous sodium hydrogencarbonate saturated solution. Then, the dichloromethane layer was added to a 50 ml of dichloromethane solution containing 2.40 g of ethylenediamine for 5 minutes while cooling with ice. Subsequently, the mixture was stirred for 2 hours at a temperature of 10° C. to 25° C.

TABLE 3

| Starting | Elemental analysis (%) | | |
|---|---|---|---|
| Compound | C | H | N |
| (3) | 52.44 | 6.12 | 12.23 |
| (5) | 54.35 | 6.45 | 11.59 |
| (10) | 59.83 | 5.70 | 10.15 |
| (18) | 60.20 | 5.85 | 9.96 | then the dichloro-methane was distilled off under reduced pressure to obtain an oily residue. The oily residue thus obtained was subjected to purification by the silica gel column chromatography (Wacogel C-200, 200 g; solvent: a 5% methanol solution in chloroform), thereby to obtain 2.48 g of N-(2-aminoethyl)-1-chloro5-isoquinolinesulfonamide, i.e., Compound (24), in a 72 % yield. Analytical data on Compound (24) are given below.

IR absorption spectrum ($cm^{-1}$): 3350,1320,1210,1160.

NMR spectrum (DCl-D$_2$O): 2.49–3.1(4H), 7.30–7.89(1H), 8.02–8.75(4H).

Substantially the same procedures as described above were repeated except that each of the compounds of the formula (IV) as set forth in Table 4-1 was used in place of ethylenediamine used above and that other reaction conditions were changed as indicated in Table 4-1. As a result, there were obtained N-(4-amino- butyl)-1-chloro-5-isoquinolinesulfonamide, i.e., Compound (25); 1-(1-chloro-5-isoquinolinesulfonyl)-3-methylpiperazine,i.e.,Compound (38); 1-(1-chloro-5-isoquinolinesulfonyl)-3-ethylpiperazine,i.e.,Compound (39); 1-(1-chloro-5-isoquinolinesulfonyl)-3-isobutyl-piperazine,i.e.,Compound (40); 1-(1-chloro-5-isoquinolinesulfonyl)-2,5-dimethylpiperazine, i.e., Compound (41); 1-(1-chloro-5-isoquinolinesulfonyl)-4methylpiperazine,i.e.,Compound (42). Analytical values of these compounds are shown in Table 4-2.

EXAMPLE 8

To 40 ml of thionyl chloride were added 2.93 g of 1-chloro-5-isoquinolinesulfonic acid as obtained in Example 1 and 0.4 ml of N,N-dimethylformamide. Then, the resulting mixture was refluxed while heating at 80° to 85° C. for 2 hours, followed by removal of the thionyl chloride and N,N-dimethylformamide under reduced pressure to obtain a residue. Then, the residue was dissolved in 50 ml of water, and the pH of the aqueous solution was adjusted to 6.0 with an aqueous sodium hydrogencarbonate saturated solution, followed by extraction twice with 50 ml of dichloromethane. The dichloromethane layer was dried with anhydrous sodium sulfate. Then, the dichloromethane was removed under reduced pressure to obtain a reaction residue, and the residue was dissolved in 30 ml of tetrahydrofuran. The solution thus obtained was added to a 30 ml of aqueous solution containing 5.73 g of 1-amidino-3-methylpiperazine sulfate for 5 minutes while cooling with ice, followed by stirring for 1 hour at a temperature of 10° C. to 25° C.

TABLE 4-1

| Run No. | 1-Chloro-5-isoquinoline-sulfonic acid | Compound (IV) | (g) | Reaction temperature (°C.) | Reaction time (hr) |
|---|---|---|---|---|---|
| 7-1 | 2.44 (g) | 1,2-diamino-ethane | 2.7 | 10–20 | 2 |
| 7-2 | 2.44 | 2-methyl-piperazine | 3.0 | 10–20 | 2 |
| 7-3 | 2.44 | 2-ethyl-piperazine | 3.4 | 10–20 | 2 |
| 7-4 | 2.44 | 2-isobutyl-piperazine | 5.7 | 10–20 | 2 |
| 7-5 | 2.44 | 2,5-dimethyl-piperazine | 3.4 | 10–20 | 2 |
| 7-6 | 2.44 | 1-methyl-piperazine | 5.0 | 10–20 | 2 |

TABLE 4-2

| Run No. | Obtained Compound | IR spectrum ($cm^{-1}$) | NMR spectrum (D$_2$O-DCl, δ) |
|---|---|---|---|
| 7-1 | (25) | 3350, 1630, 1210, 1150 | 1.7–2.2(4H), 2.5–3.2(4H), 7.3–7.9(1H), 7.9–8.8(4H) |
| 7-2 | (38) | 1610, 1360, 1150 | 1.1–1.3(3H), 3.6–4.2(7H), 7.6–7.9(1H), 8.1–8.3(4H) |
| 7-3 | (39) | 1610, 1350, 1150 | 0.8–1.1(3H), 1.3–1.6(2H), 3.5–4.2(7H), 7.5–7.8(1H), 8.1–8.3(4H) |
| 7-4 | (40) | 1620, 1360, 1150 | 0.9–1.0(6H), 1.4–1.8(3H), 3.4–4.1(7H), 7.6–7.9(1H), 8.1–8.3(4H) |
| 7-5 | (41) | 1620, 1360, 1150 | 1.0–1.3(6H), 3.3–4.5(6H), 7.6–7.9(1H), 8.1–8.3(4H) |
| 7-6 | (42) | 1610, 1360, 1150 | 2.4(3H), 3.3–4.2(8H), 7.6–7.9(1H), 8.1–8.4(4H) |

Then the reaction mixture was condensed under reduced pressure to obtain an oily residue. To the oily residue thus obtained was added 20 ml of 0.1N hydrochloric acid, followed by stirring and filtration to obtain an aqueous solution. The pH of the aqueous solution was adjusted to 12.5 with a 1N sodium hydroxide solution to precipitate crystals. The crystals were separated by filtration, washed with 20 ml of water, 20 ml of methanol and then 10 ml of ether, and dried under reduced pressure to obtain 3.00 g of 1-(1-chloro-5-isoquinolinesulfonyl)-4-amidino-2-methylpiperazine, i.e., Compound (45), in a 68% yield. Analytical data on Compound (45) are given below.

IR absorption spectrum ($cm^{-1}$): 1690,1650,1240

NMR spectrum (D$_2$O-DCl): 1.4–1.7 (3H), 3.5–4.3 (7H), 7.6–7.9(1H), 8.0–8.3(4H).

Substantially the same procedures as described above were repeated except that each of the compounds of the formula (IV) as set forth in Table 5-1 was used in place of 1-amidino-3-methylpiperazine sulfate used above and that other reaction conditions were changed as indicated in Table 5-1. As a result, there were obtained N-(3-guanidino-2-methylpropyl)-1-chloro-5-isoquinolinesulfonamide, i.e., Compound (36); N-(4-guanidino-3-methylbutyl)-1-chloro-5-isoquinolinesulfonamide, i.e., Compound (37); 1-(1-chloro-5-isoquinolinesulfonyl)-4-amidinopiperazine, i.e., Compound (43); 1-(1-chloro-5-isoquinolinesulfonyl)-4-amidinohomopiperazine, i.e., Compound (44); 1-(1-chloro-5-isoquinolinesulfonyl)-4-amidino-2,5-dimethylpiperazine, i.e., Compound (46). The yield and analytical values of these compounds are shown in Table 5-2.

EXAMPLE 9

To 50 ml of thionyl chloride were added 5.86 g of 1-chloro-5-isoquinolinesulfonic acid as obtained in Example 1 and 0.5 ml of N,N-dimethylformamide. Then, the resulting mixture was refluxed while heating at 80° to 85° C. for 2 hours, followed by removal of the thionyl chloride and N,N-dimethylformamide under reduced pressure to obtain a residue. The thus obtained residue was dissolved in 50 ml of water, and the pH of the aqueous solution was adjusted to 6.0 with an aqueous sodium hydrogencarbonate saturated solution, followed by extraction twice with 50 ml of dichloromethane.

TABLE 5-1

| Run No. | 1-Chloro-5-isoquinoline-sulfonic acid (g) | Compound (IV).½ Sulfate | (g) | Reaction Temperature (°C.) | Reaction time (hr) |
|---|---|---|---|---|---|
| 8-1 | 2.44 | 3-Guanidino-2-methylpropyl amine | 5.4 | 20-30 | 1 |
| 8-2 | 2.44 | 4-Guanidino-3-methyl-butylamine | 6.0 | 20-30 | 1 |
| 8-3 | 2.44 | 1-Amidino-piperazine | 5.3 | 20-30 | 3 |
| 8-4 | 2.44 | 1-Amidinohomo-piperazine | 5.8 | 20-30 | 3 |
| 8-5 | 2.44 | 1-Amidino-2,5-dimethyl-piperazine | 6.2 | 20-30 | 3 |

TABLE 5-2

| Run No. | Obtained Compound | Yield | IR spectrum (cm$^{-1}$) | NMR spectrum (D$_2$O-DCl) |
|---|---|---|---|---|
| 8-1 | (36) | 2.7 g 76% | 1650, 1360 1150 | 1.2-1.4(3H), 1.8-4.2(5H) 7.3-7.9(1H), 7.9-8.8(4H) |
| 8-2 | (37) | 2.6 g 71% | 1640, 1360 1150 | 1.2-1.9(6H), 3.6-4.4(4H) 7.6-7.9(1H), 8.1-8.3(4H) |
| 8-3 | (43) | 2.9 g 83% | 1640, 1350 1150 | 3.6-4.5(8H), 7.6-7.9(1H) 8.1-8.3(4H) |
| 8-4 | (44) | 3.0 g 81% | 1650, 1360 1150 | 2.1-2.7(2H), 3.6-4.4(8H) 7.6-7.9(1H), 8.1-8.4(4H) |
| 8-5 | (46) | 2.8 g 74% | 1640, 1335 1150 | 1.1-1.5(6H), 3.3-4.6(6H) 7.5-8.0(1H), 8.1-8.3(4H) |

The dichloromethane layer was added to a 50 ml of dichloromethane solution containing 7.31 g of 1-benzyloxycarbonylamino-2-aminopropane and 3.03 g of triethylamine for 5 minutes while cooling with ice, followed by stirring for 1 hour at a temperature of 10° C. to 20° C. The reaction mixture thus obtained was washed twice with diluted hydrochloric acid (pH 3), dried with anhydrous sodium sulfate and then distilled under reduced pressure to obtain an oily residue (Compound of the formula (VI)). To the oily residue thus obtained were added 150 ml of methanol and 0.5 g of 5% palladium-charcoal, followed by stirring for 5 hours at a temperature of 15° C. to 25° C. under a hydrogen atmosphere(40 psi) to effect reductive cleavage. The reaction mixture was filtrated and the obtained filtrate was condensed under reduced pressure to obtain an oily residue. The oily residue thus obtained was subjected to purification by the silica gel column chromatography (Wacogel C-200, 200 g; solvent: a 10% methanol solution in chloroform), thereby to obtain 4.86 g of N-(2-amino-1-methylethyl)-1-chloro-5-isoquinolinesulfonamide, i.e., Compound (26), in a 68% yield. Analytical data on Compound (26) are given below.

IR absorption spectrum (cm$^{-1}$): 3360, 1620, 1320, 1210, 1160.

NMR spectrum (DCl-D$_2$O): 1.2-1.5 (3H), 3.4-4.4 (3H), 7.30-7.89 (1H), 8.02-8.75 (4H).

Substantially the same procedures as described above were repeated except that each of the compounds of the formula (V) as set forth in Table 6-1 was used in place of 1-benzyloxycarbonylamino-2-aminopropane and that other reaction conditions were changed as indicated in Table 6-1. As a result, there were obtained N-(1-aminomethylpentyl)-1-chloro-5-isoquinolinesulfonamide, i.e., Compound (27); N-(2-amino-3-methylbutyl)-1-chloro-5-isoquinolinesulfonamide, i.e., Compound (28). The yields and analytical values of these compounds are shown in Table 6-2.

EXAMPLE 10

In 50 ml of water were dissolved 3.0 g of N-(2-amino-1-methylethyl)-1-chloro-5-isoquinolinesulfonamide (Compound (26)) as obtained in Example 9, 4.17 g of S-methylisothiourea sulfate and 1.2 g of sodium hydroxide. The resulting mixture was stirred for 2 hours at a temperature of 60° C., and then cooled in an ice bath to precipitate crystals, followed by separation of the crystals by filtration.

TABLE 6-1

| Run No. | 1-Chloro-5-isoquinoline-sulfonic acid (g) | Compound (V) | (g) | Triethylamine (g) | Reaction time for preparing compound (VI) (hr) | Hydrogen atomosphere (psi) | Time for reductive cleavage (hr) |
|---|---|---|---|---|---|---|---|
| 9-1 | 3.66 | 2-Amino-6-benzyloxycar-bonylaminohexane | 5.63 | 2.3 | 2 | 50 | 10 |
| 9-2 | 3.66 | 2-Benzyloxycarbonyl-amino-3-methyl-butylamine | 5.31 | 2.3 | 2 | 50 | 10 |

TABLE 6-2

| Run No. | Obtained Compound | Yield | IR spectrum (cm$^{-1}$) | NMR spectrum (D$_2$O-DCl) |
|---|---|---|---|---|
| 9-1 | (27) | 3.5 g (69%) | 3360, 1610, 1320, 1260, 1150 | 0.8-2.0(9H), 2.8-4.5(3H) 7.5-7.7(1H), 8.0-8.3(4H) |
| 9-2 | (28) | 4.0 g (81%) | 3350, 1600, 1320, 1200, 1150 | 1.0-1.7(7H), 2.8-4.7(3H) 7.5-7.7(1H), 8.0-8.3(4H) |

The crystalline residue thus obtained was washed with water to obtain 3.25 g of N-(2-guanidino-1-methylethyl)-1-chloro-5-isoquinolinesulfonamide, i.e., Compound (33) in a 95% yield. Analytical data on Compound (33) are given below.

IR absorption spectrum (cm$^{-1}$): 1690, 1640, 1320, 1160.

NMR spectrum (DCl-D$_2$O); 1.4-1.9 (3H), 3.5-4.6 (3H), 7.30-7.89 (1H), 8.02-8.75 (4H).

Substantially the same procedures as described above were repeated except that each of the compounds of the formula (VII) obtained in Examples 7 and 9 as set forth in Table 7-1 was used as a starting compound in place of Compound (26) used above and that other reaction conditions were changed as indicated in Table 7-1. As a result, there were obtained N-(2-guanidino- ethyl)-1- chloro-5-isoquinolinesulfonamide, i.e., Compound (31); N-(4-guanidinobutyl)-1-chloro-5isoquinolinesulfonamide, i.e., Compound (32); N-(1-guanidinomethylpentyl)-1-chloro-5-isoquinolinesulfonamide, i.e., Compound (34); N-(2-guanidino-3-methyl- butyl)-1-chloro-5-isoquinolinesulfonamide, i.e., Compound (35). The yields and analytical values of these compounds are shown in Table 7-2.

TABLE 7-1

| Run No. | Starting Compound | (g) | S—methyl-isothiourea-sulfate (g) | NaOH (g) | Reaction temperature (°C.) | Reaction time (hr) |
|---|---|---|---|---|---|---|
| 10-1 | (24) | 4.3 | 6.5 | 1.8 | 60 | 3 |
| 10-2 | (25) | 3.1 | 4.5 | 1.2 | 60 | 3 |
| 10-3 | (27) | 3.4 | 4.5 | 1.2 | 80 | 5 |
| 10-4 | (28) | 3.3 | 4.5 | 1.2 | 80 | 8 |

TABLE 7-2

| Run No. | Obtained Compound | Yield | IR spectrum (cm$^{-1}$) | NMR spectrum (D$_2$O-DCl) |
|---|---|---|---|---|
| 10-1 | (31) | 4.4 g (90%) | 1690, 1640 1350, 1150 | 2.6–3.8(4H), 7.3–7.9(1H) 8.0–8.8(4H) |
| 10-2 | (32) | 3.0 g (85%) | 1630, 1360 1150 | 1.7–2.2(4H), 2.5–3.2(4H) 7.3–7.5(1H), 7.9–8.8(4H) |
| 10-3 | (34) | 3.1 g (81%) | 1640, 1360 1150 | 0.8–2.0(9H), 3.0–4.3(3H) 7.3–7.5(1H), 7.9–8.8(4H) |
| 10-4 | (35) | 2.8 g (75%) | 1630, 1360 1150 | 0.8–1.6(7H), 3.1–4.2(3H) 7.3–7.5(1H), 8.0–8.8(4H) |

EXAMPLE 11

To 50 ml of thionyl chloride were added 5.85 g of 1-chloro-5-isoquinolinesulfonic acid as obtained in Example 1 and 0.5 ml of N,N-dimethylformamide. Then, the resulting mixture was refluxed while heating for 2 hours, followed by removal of the thionyl chloride and N,N-dimethylformamide under reduced pressure to obtain a residue. Then, the residue was dissolved in 50 ml of water, and the pH of the aqueous solution was adjusted to 6.0 with an aqueous sodium hydrogencarbonate saturated solution, followed by extraction twice with 50 ml of dichloromethane. The dichloromethane layer was added to a 50 ml of dichloromethane solution containing 1.84 g of ethanolamine and 3.03 g of triethylamine for 5 minutes while cooling with ice. Then, the mixture was stirred for 1 hour at a temperature of 10° C. to 20° C. The thus obtained reaction mixture was washed thrice with water, dried with anhydrous sodium sulfate and then distilled under reduced pressure to obtain 5.04 g of N-(2-hydroxy- ethyl)-1-chloro-5-isoquinolinesulfonamide in a 96% yield.

To 40 ml of a pyridine solution containing 2.63 g of N-(2-hydroxyethyl)-1-chloro-5-isoquinolinesulfonamide as obtained above was added 3.81 g of p-toluenesulfonyl chloride while cooling with ice. The solution thus obtained was stirred for 24 hours at a temperature of 5° C. and poured into 100 g of ice water followed by extraction twice with 100 ml of dichloromethane. The dichloromethane layer was dried with anhydrous sodium sulfate and condensed under reduced pressure to obtain 4.32 g of N-(2-p-toluenesulfonyloxyethyl)-1-chloro-5-isoquinolinesulfonamide.

4 g of the thus obtained N-(2-p-toluenesulfonyl- oxyethyl)-1-chloro-5-isoquinolinesulfonamide and 1 ml of a 40% methylamine solution in methanol were put in 50 ml of dichloromethane and heated for 4 hours at 70° C. in a sealed bottle. After cooling, the reaction mixture was condensed under reduced pressure to obtain an oily residue. The oily residue thus obtained was subjected to purification by the silica gel column chromatography (Wacogel C-200, 100 g; solvent: a 10% methanol solution in chloroform) to obtain 4.86 g of N-(2-methylaminoethyl)-1-chloro-5-isoquinolinesulfonamide, i.e., Compound (70), in a 79% yield. Analytical data on Compound (70) are given below.

IR absorption spectrum (cm$^{-1}$): 3350, 1620, 1320, 1160.

NMR spectrum (DCl–D$_2$O): 3.1 (3H), 3.4–4.1 (4H), 7.3–7.7 (1H), 8.1–8.7 (4H).

EXAMPLE 12

10 g of N-(2-aminoethyl)-1-chloro-5-isoquinolinesulfonamide (Compound (24)) as obtained in Example 7 was mixed with 100 ml of 6 N-hydrochloric acid, and the mixture was stirred for 6 hours at a temperature of 65° C. to precipitate crystals. The crystals were separated by filtration, washed with water and ethanol to obtain 8.94 g of N-(2-aminoethyl)-1-hydroxy-5-isoquinolinesulfonamide hydrochloride, i.e., Compound (47), in a 84% yield. Analytical data on Compound (47) are given below.

IR absorption spectrum (cm$^{-1}$): 3300, 1690, 1630, 1160.

NMR spectrum (CD$_3$ SOCD$_3$+CD$_3$OD): 2.8–3.3 (4H), 7.2–8.8 (5H).

Elemental analysis (%): (Calculated) C: 43.50, H: 4.65, N: 13.83. (Found) C: 43.29, H: 4.90, N: 13.79.

Substantially the same procedures were repeated except that the starting compounds of the formula (XV) as indicated in Table 8-1 were used in place of Compound (24) used above and that some other reaction conditions were changed as set forth in Table 8-1. As a result, there were obtained N-(4-aminobutyl)-1-hydroxy-5-isoquinolinesulfonamide, i.e., Compound (48); N-(2-amino 1-methylethyl)-1-hydroxy-5-isoquinolinesulfonamide, i.e., Compound (49); N-(1-amino methylpentyl)-1-hydroxy-5-isoquinolinesulfonamide, i.e., Compound (50); N-(2-amino-3-methylbutyl)-1-hydoxy-5-isoquinolinesulfonamide, i.e., Compound (51); N-(2-guanidinoethyl)-1-hydroxy-5-isoquinolinesulfonamide, i.e., Compound (54); N-(4-guanidinobutyl)-1-hydroxy-5-isoquinolinesulfonamide, i.e., Compound (55); N-(2-guanidino-1-methylethyl)-1-hydroxy-5-isoquinolinesulfonamide, i.e., Compound (56); N-(1-guanidinomethylpentyl)-1-hydroxy-5-isoquinolinesulfonamide, i.e., Compound (57); N-(2-guanidino-3-methylbutyl)-1-hydroxy-5-isoquinolinesulfonamide, i.e., Compound (58); N-(3-guanidino-2-methylpropyl)-1-hydroxy-5-isoquinolinesulfonamide, i.e., Compound (59); N-(3-guanidino-3-methylbutyl)-1-hydroxy-5-isoquinolinesulfonamide, i.e. Compound (60); 1-(1-hydroxy-5-isoquinolinesulfonyl)-3-methylpiperazine, i.e. Compound (61); 1-(1-hydroxy-5-isoquinolinesulfonyl)-3-ethylpiperazine, i.e., Compound (62); 1-(1-hydroxy-5-isoquinolinesulfonyl)-3-isobutylpiperazine, i.e., Compound (63); 1-(1-hydroxy-5-isoquinolinesulfonyl)-2,5-dimethylpiperazine, i.e., Compound (64); 1-(1-hydroxy-5-isoquinolinesulfonyl)-4-methylpiperazine, i.e. Compound (65); 1-(1-hydroxy-5-isoquinolinesulfonyl)-4-amidinopiperazine, i.e., Compound (66); 1-(1-hydroxy-5-isoquinolinesulfonyl)-4-amidinohomopiperazine, i.e., Compound (67); 1-(1-hydroxy-5-isoquinolinesulfonyl)-4-amidino-2-methylpiperazine, i.e., Compound (68); 1-(1-hydroxy-5- isoquinolinesulfonyl)-4-amidino-2,5-dimethylpiperazine, i.e., Compound (69). The yields and analytical values of these compounds are shown in Table 8-2.

EXAMPLE 13

To 50 ml of thionyl chloride were added 5.86 g of 1-chloro-5-isoquinolinesulfonic acid as obtained in Example 1 and 0.5 ml of N,N-dimethylformamide. Then, the resulting mixture was refluxed while heating at 80° to 85° C. for 2 hours, followed by removal of the thionyl chloride and N,N-dimethylformamide under reduced pressure to obtain a residue. The thus obtained residue was dissolved in 50 ml of water, and the pH of the aqueous solution was adjusted to 6.0 with an aqueous sodium hydrogencarbonate saturated solution, followed by extraction twice with 50 ml of dichloromethane.

TABLE 8-1

| Run No. | Starting Compound (XV) | (g) | 6N—HCl (ml) | Reaction temperature (°C.) | Reaction time (hr) |
|---|---|---|---|---|---|
| 12-1 | (25) | 3.1 | 30 | 80 | 3 |
| 12-2 | (26) | 3.0 | 30 | 80 | 3 |
| 12-3 | (27) | 3.4 | 30 | 70 | 3 |
| 12-4 | (28) | 3.3 | 30 | 70 | 5 |
| 12-5 | (31) | 3.3 | 30 | 80 | 3 |
| 12-6 | (32) | 3.6 | 30 | 70 | 5 |
| 12-7 | (33) | 3.4 | 30 | 70 | 10 |
| 12-8 | (34) | 3.8 | 30 | 70 | 10 |
| 12-9 | (35) | 3.7 | 30 | 70 | 5 |
| 12-10 | (36) | 3.6 | 30 | 80 | 15 |
| 12-11 | (37) | 3.7 | 30 | 80 | 15 |
| 12-12 | (38) | 3.3 | 30 | 70 | 15 |
| 12-13 | (39) | 3.4 | 30 | 70 | 10 |
| 12-14 | (40) | 3.7 | 30 | 70 | 10 |
| 12-15 | (41) | 3.4 | 30 | 70 | 10 |
| 12-16 | (42) | 3.3 | 30 | 80 | 5 |
| 12-17 | (43) | 3.5 | 30 | 80 | 10 |
| 12-18 | (44) | 3.7 | 30 | 80 | 5 |
| 12-19 | (45) | 3.7 | 30 | 80 | 5 |
| 12-20 | (46) | 3.8 | 30 | 80 | 5 |

TABLE 8-2

| Run No. | Obtained Compound | Yield (g) | Yield (%) | Elemental analysis (%) C | H | N |
|---|---|---|---|---|---|---|
| 12-1 | (48) | 2.7 | 81 | 47.11 | 5.42 | 12.38 |
| 12-2 | (49) | 2.5 | 78 | 45.16 | 5.13 | 13.04 |
| 12-3 | (50) | 3.0 | 83 | 49.87 | 6.14 | 11.71 |
| 12-4 | (51) | 2.9 | 85 | 48.46 | 5.67 | 12.03 |
| 12-5 | (54) | 2.9 | 83 | 41.56 | 4.51 | 20.06 |
| 12-6 | (55) | 2.6 | 71 | 44.87 | 5.15 | 18.81 |
| 12-7 | (56) | 2.8 | 79 | 43.21 | 5.24 | 19.61 |
| 12-8 | (57) | 3.0 | 75 | 47.72 | 6.02 | 17.50 |
| 12-9 | (58) | 3.1 | 81 | 46.32 | 5.68 | 18.01 |
| 12-10 | (59) | 3.7 | 73 | 44.93 | 5.28 | 18.50 |
| 12-11 | (60) | 2.9 | 75 | 46.21 | 5.38 | 18.10 |
| 12-12 | (61) | 2.6 | 77 | 48.91 | 5.31 | 12.31 |
| 12-13 | (62) | 3.0 | 85 | 50.25 | 5.72 | 11.74 |
| 12-14 | (63) | 2.7 | 71 | 52.90 | 6.03 | 10.91 |
| 12-15 | (64) | 2.5 | 70 | 50.45 | 5.81 | 11.71 |
| 12-16 | (65) | 2.7 | 79 | 48.81 | 5.03 | 12.41 |
| 12-17 | (66) | 2.6 | 69 | 45.00 | 4.81 | 18.72 |
| 12-18 | (67) | 2.8 | 73 | 46.80 | 5.12 | 18.16 |
| 12-19 | (68) | 2.8 | 74 | 46.69 | 5.32 | 18.20 |

TABLE 8-2-continued

| Run No. | Obtained Compound | Yield (g) | Yield (%) | Elemental analysis (%) C | H | N |
|---|---|---|---|---|---|---|
| 12-12 | (69) | 3.0 | 75 | 48.11 | 5.68 | 17.63 |

The dichloromethane layer was added to 100 ml of a dichloromethane solution containing 6.1 g of N-(2-aminoethyl)-N-t-butoxycarbonylhexylamine and 3.0 g of triethylamine for 20 minutes while cooling with ice. The thus obtained mixture was stirred for 1 hour at a temperature of 15° C. to 20° C. Then, the reaction mixture was washed twice with 50 ml of water, dried with anhydrous sodium sulfate and then distilled under reduced pressure to obtain an oily residue. To the oily residue thus obtained was added 10 ml of trifluoroacetic acid while cooling with ice, followed by stirring for 1 hour at a temperature of 15° C. to 20° C. To the obtained reaction mixture was added 10 ml of ice water, and the pH of the aqueous solution was adjusted to 10 with 5% aqueous sodium hydroxide solution, followed by extraction twice with 50 ml of dichloromethane. The dichloromethane layer was washed with water, dried with anhydrous sodium sulfate and then distilled under reduced pressure to obtain an oily residue. The thus obtained oily residue was subjected to purification by the silica gel column chromatography (Wacogel C-200, 100 g; solvent: a 3% methanol solution in chloroform), thereby to obtain 6.1 g of N-(2-hexylaminoethyl)-1-chloro-5-isoquinolinesulfonamide, i.e., Compound (74), in a 81% yield.

Analytical data on Compound (74) are given below.
IR absorption spectrum (cm$^{-1}$): 3400, 1330, 1160.
NMR spectrum (DCl-D$_2$O): 0.6–2.0 (11H), 2.4–3.5 (6H) 7.5–8.0 (1H), 8.1–8.8 (4H).

Substantially the same procedures as described above were repeated except that each of compounds of the formula (V) as set forth in Table 9-1 was used in place of N-(2-aminoethyl)-N-t-butoxycarbonylhexylamine and that other reaction conditions were changed as indicated in Table 9-1. As a result, there were obtained N-(2-ethylaminoethyl)-1-chloro-5-isoquinolinesulfonamide, i.e., Compound (71); N-(2-propylaminoethyl)-1-chloro-5-isoquinolinesulfonamide, i.e., Compound (72); N-(2-butylaminoethyl)-1-chloro-5-isoquinolinesulfonamide, i.e., Compound (73). The yields and analytical values of these compounds are shown in Table 9-2.

EXAMPLE 14

4 g of N-(2-hexylaminoethyl)-1-chloro-5-isoquinolinesulfonamide (Compound (74)) as obtained in Example 13 was mixed with 50 ml of 6 N-hydrochloric acid and the resulting mixture was stirred for 6 hours at a temperature of 65° C. Then, the reaction mixture was allowed to cool for 2 hours to precipitate crystals.

TABLE 9-1

| Run No. | 1-Chloro-5-isoquinoline-sulfonic acid (g) | Compound (V) H$_2$N–––N–COO—t-Bu / R$^3$ | | (g) | Triethylamine (g) | Reaction temperature (°C.) | CF$_3$COOH (ml) | Reaction temperature (°C.) | Reaction time (hr) |
|---|---|---|---|---|---|---|---|---|---|
| 13-1 | 3.66 | R$^3$: | C$_2$H$_5$ | 4.2 | 2.5 | 10–15 | 20 | 20–25 | 2 |
| 13-2 | 3.66 | R$^3$: | C$_3$H$_7$ | 4.5 | 2.5 | 10–15 | 20 | 20–25 | 3 |
| 13-3 | 3.66 | R$^3$: | C$_4$H$_9$ | 5.0 | 2.5 | 10–15 | 20 | 20–25 | 3 |

TABLE 9-2

| Run No. | Obtained Compound | Yield | IR spectrum (cm$^{-1}$) | NMR spectrum (CD$_3$OD-DCl) |
|---|---|---|---|---|
| 1 | (71) | 3.7 g (79%) | 3350, 1610 1330, 1150 | 0.9–1.5(3H), 2.5–4.0(6H) 7.5–7.7(1H), 8.0–8.7(4H) |
| 2 | (72) | 3.9 g (80%) | 3400, 1600 1340, 1150 | 0.8–2.0(5H), 2.5–4.3(6H) 7.5–7.7(1H), 8.0–8.8(4H) |
| 3 | (73) | 3.8 g (75%) | 3400, 1600 1330, 1160 | 0.8–2.0(7H), 2.5–4.5(6H) 7.5–7.7(1H), 8.0–8.8(4H) |

The crystals were separated by filtration, and then recrystallized from ethanol to give 3.1 g of N-(2-hexylaminoethyl)-1-hydroxy-5-isoquinolinesulfonamide hydrochloride, i.e., Compound (81), in a 74% yield. Analytical data on Compound (81) are given below.

IR absorption spectrum (cm$^{-1}$): 3300, 1685, 1630, 1160.

NMR spectrum (DCl-D$_2$O): 0.6–2.0 (11H), 2.5–4.0 (6H), 7.5–8.0 (1H), 8.0–9.0 (4H).

EXAMPLE 15

To 50 ml of thionyl chloride were added 5.85 g of 1-chloro-5-isoquinolinesulfonic acid as obtained in Example 1 and 0.5 ml of N,N-dimethylformamide. Then, the resulting mixture was refluxed while heating at 80° to 85° C. for 2 hours, followed by removal of the thionyl chloride and N,N-dimethylformamide under reduced pressure to obtain a residue. The residue was dissolved in a liquid consisting of 20 ml of water and 50 ml of dichloromethane, and the pH of the aqueous solution was adjusted to 6.0 with an aqueous sodium hydrogencarbonate saturated solution. Then, the dichloromethane layer was added to a 100 ml of a dichloromethane solution containing 6.0 g of homopiperazine for 20 minutes while cooling with ice, followed by stirring for 1 hour at a temperature of 15° C. to 20° C. The obtained reaction mixture was washed thrice with 50 ml of water, dried with anhydrous sodium sulfate and then distilled under reduced pressure to obtain oily residue. The thus obtained oily residue was subjected to purification by the silica gel column chromatography (Wacogel C-200, 150 g; solvent: a 5% methanol solution in chloroform), thereby to obtain 5.5 g of 1-(1-chloro-5-isoquinolinesulfonyl)homopiperazine, i.e., Compound (76), in a 84% yield. Analytical data on Compound (76) are given below.

IR absorption spectrum (cm-1): 3400, 1330, 1140.

NMR spectrum ((CD$_3$)$_2$SO-CD$_3$OD): 1.7–2.3 (2H), 3.1–3.7 (8H), 7.2–7.7 (1H), 7.7–8.8 (4H).

EXAMPLE 16

Substantially the same procedures as in Example 15 were repeated except that 5.16 g of piperazine was used in place of 6.0 g of homopiperazine. As a result, there was obtained 5.5 g of 1-(1-chloro-5-isoquinolinesulfonyl)piperazine, i.e., Compound (75), in a 88% yield. Analytical data on Compound (75) are given below.

IR absorption spectrum (cm-1): 3360, 1350, 1160, 1140.

NMR spectrum (CD$_3$)$_2$SO-CD$_3$OD): 2.8–3.8 (8H), 7.5–8.0 (1H), 7.7–8.8 (4H).

EXAMPLE 17

9.7 g of 1-(1-chloro-5-isoquinolinesulfonyl)homopiperazine (Compound (76)) as obtained in substantially the same manner as in Example 15 was mixed with 100 ml of 6N hydrochloric acid, and the mixture was stirred for 6 hours at a temperature of 65° C. to precipitate crystals. Then, the crystals were separated by filtration, and washed with water and then ethanol to obtain 6.9 g of 1-(1-hydroxy-5-isoquinolinesulfonyl)homopiperazine, i.e., Compound (83), in a 67% yield. Analytical data on Compound (83) are given below.

IR absorption spectrum (cm-1): 3300, 1690, 1630, 1340, 1160.

NMR spectrum (DCl-D$_2$O): 1.7–2.3 (2H), 3.1–3.7 (8H), 7.2–7.7 (1H), 7.7–8.8 (4H).

EXAMPLE 18

In substantially the same manner as in the above Example, various compounds of the present invention were prepared. These compounds are 1-(5-isoquinolinesulfonyl)-3-propylhomopiperazine, i.e., Compound (8); 1-(5-isoquinolinesulfonyl)-3-benzylhomopiperazine, i.e., Compound (11); 1-(5-isoquinolinesulfonyl)-6-butylhomopiperazine, i.e., Compound (14); 1-(5-isoquinolinesulfonyl)-6-pentylhomopiperazine, i.e., Compound (15); 1-(5-isoquinolinesulfonyl)-6-phenylhomopiperazine, i.e., Compound (17); 1-(5-isoquinolinesulfonyl)-4-propylhomopiperazine, i.e., Compound (21); N-(3-di-n-butylaminopropyl)-1-chloro-5-isoquinolinesulfonamide, i.e., Compound (29); N-[2-(N-cyclohexyl-N-methylamino)ethyl]-1-chloro-5-isoquinolinesulfonamide, i.e., Compound (30); N-(3-di-n-butylaminopropyl)-1-hydroxy-5-isoquinolinesulfonamide, i.e., Compound (52); N-[2-(N-cyclohexyl-N-methylamino)ethyl]-1-hydroxy-5-isoquinolinesulfonamide, i.e., Compound (53); N-(2-methylaminoethyl)-1-hydroxy-5-isoquinolinesulfonamide, i.e., Compound (77); N-(2-ethylaminoethyl)-1-hydroxy-5-isoquinolinesulfonamide, i.e., Compound (78); N-(2-propylaminoethyl)-1-hydroxy-5-isoquinolinesulfonamide, i.e., Compound (79); N-(2-butylaminoethyl)-1-hydroxy-5-isoquinolinesulfonamide, i.e., Compound (80); 1-(1-hydroxy-5-isoquinolinesulfonyl)piperazine, i.e., Compound (82). Of them, Compounds (8) to (17) were prepared in substantially the same manner as in Example 4, Compound (21) Example 5, Compounds (29) and (30) Example 7, and Compounds (52) to (82) Example 17.

Analytical data on these compounds are given in Tables 10-1 and 10-2.

APPLICATION EXAMPLE 1

Effect of the compounds of the present invention on relaxation of mesenteric artery was examined according to the method as mentioned hereinbefore. The obtained ED$_{50}$ values are shown in Table 11.

APPLICATION EXAMPLE 2

Effect of the compounds of the present invention on reduction of blood pressure was examined according to the method as mentioned hereinbefore. The obtained maximally reduced blood pressures (ΔPmax, mmHg) are shown in Tables 12-1 and 12-2.

TABLE 10-1

| Obtained Compound | IR spectrum (cm$^{-1}$) | NMR spectrum (D$_2$O-DCl) |
|---|---|---|
| (8) | 3330, 1600 1340, 1160 | 0.5–3.0(9H), 7.6–7.9(1H), 8.1–8.8 (4H), 9.3(1H) |
| (11) | 3330, 1620 1330, 1150 | 2.1–2.7(4H), 3.6–4.5(7H), 7.2(5H), 7.6–7.9(1H), 8.1–8.8(4H), 9.3(1H) |
| (14) | 3330, 1610 1330, 1150 | 0.7–3.0(10H), 3.6–4.4(8H), 7.6–7.9 (1H), 8.1–8.8(4H), 9.3(1H) |

TABLE 10-1-continued

| Obtained Compound | IR spectrum (cm$^{-1}$) | NMR spectrum (D$_2$O-DCl) |
|---|---|---|
| (15) | 3330, 1620 1340, 1160 | 0.7–3.3(12H), 3.5–4.5(8H), 7.6–7.9 (1H), 8.1–8.8(4H), 9.3(1H) |
| (17) | 3330, 1600 1340, 1150 | 2.0–3.3(1H), 3.5–4.5(8H), 7.2(5H), 7.6–7.9(1H), 8.1–8.8(4H), 9.3(1H) |
| (21) | 3330, 1610 1340, 1150 | 0.8–3.0(7H), 3.3–4.7(10H), 7.6–7.9 (1H), 8.1–8.8(4H), 9.3(1H) |
| (29) | 3330, 1600 1340, 1160 | 0.7–3.0(16H), 3.2–4.5(8H), 7.6–7.9 (1H), 8.1–8.8(4H), 9.3(1H) |
| (30) | 3330, 1600 1340, 1150 | 0.7–2.8(12H), 3.0(3H), 3.5–4.5 (6H), 7.6–7.9(1H), 8.1–8.8(4H), 9.3(1H) |

TABLE 10-2

| Obtained Compound | Elemental analysis (%) | | |
|---|---|---|---|
| | C | H | N |
| (52) | 55.97 | 7.66 | 9.79 |
| (53) | 54.98 | 6.98 | 10.20 |
| (77) | 45.53 | 5.01 | 13.20 |
| (78) | 47.18 | 5.49 | 12.50 |
| (79) | 48.65 | 6.03 | 12.06 |
| (80) | 50.21 | 6.33 | 11.55 |
| (82) | 47.44 | 5.00 | 12.75 |

TABLE 11

| Compound No. | ED$_{50}$ (μM) | Compound No. | ED$_{50}$ (μM) |
|---|---|---|---|
| (1) | 0.8 | (43) | 2 |
| (2) | 4 | (44) | 4 |
| (3) | 1.6 | (45) | 3 |
| (4) | 1.6 | (46) | 5 |
| (5) | 8 | (47) | 10 |
| (6) | 10 | (48) | 15 |
| (7) | 6 | (49) | 14 |
| (9) | 4 | (50) | 7 |
| (10) | 12 | (51) | 20 |
| (12) | 3 | (52) | 21 |
| (13) | 11 | (53) | 17 |
| (16) | 12 | (54) | 18 |
| (18) | 10 | (55) | 13 |
| (19) | 8 | (56) | 14 |
| (20) | 11 | (57) | 11 |
| (22) | 13 | (58) | 15 |
| (23) | 12 | (59) | 21 |
| (24) | 5 | (60) | 23 |
| (25) | 7 | (61) | 17 |
| (26) | 4 | (62) | 25 |
| (27) | 4 | (63) | 18 |
| (28) | 10 | (64) | 21 |
| (29) | 11 | (65) | 25 |
| (30) | 13 | (66) | 4 |
| (31) | 2 | (67) | 6 |
| (32) | 4 | (68) | 9 |
| (33) | 4 | (69) | 8 |
| (34) | 8 | (71) | 12 |
| (35) | 8 | (72) | 11 |
| (36) | 7 | (73) | 8 |
| (37) | 11 | (74) | 2 |
| (38) | 17 | (75) | 1 |
| (39) | 18 | (76) | 2 |
| (40) | 13 | (81) | 6 |
| (41) | 14 | (83) | 3 |
| (42) | 21 | | |

TABLE 12-1

| Compound No. | Dosage (mg/kg) | ΔPmax (mmHg) | Compound No. | Dosage (mg/kg) | ΔPmax (mmHg) |
|---|---|---|---|---|---|
| (1) | 100 | 80 | (48) | 100 | 51 |
| (3) | " | 65 | (49) | 50 | 33 |
| (18) | " | 43 | (50) | " | 28 |
| (24) | 50 | 70 | (51) | " | 71 |
| (25) | 100 | 50 | (52) | " | 65 |
| (26) | 50 | 53 | (53) | " | 56 |
| (27) | " | 45 | (54) | 100 | 40 |
| (28) | " | 58 | (55) | " | 38 |
| (29) | " | 43 | (56) | " | 45 |
| (30) | " | 54 | (57) | " | 38 |
| (31) | 100 | 40 | (58) | " | 41 |
| (32) | " | 38 | (59) | " | 52 |
| (33) | " | 51 | (60) | " | 61 |
| (34) | " | 45 | (61) | " | 48 |
| (35) | " | 33 | (62) | " | 36 |
| (36) | " | 48 | (63) | " | 48 |
| (37) | " | 31 | (64) | " | 65 |
| (38) | " | 45 | (65) | " | 53 |
| (39) | " | 48 | (66) | " | 43 |
| (40) | " | 51 | (67) | " | 44 |
| (41) | " | 39 | (68) | " | 48 |
| (42) | " | 56 | (69) | " | 51 |
| (43) | " | 32 | (74) | " | 45 |
| (44) | " | 25 | (76) | " | 60 |
| (45) | " | 37 | (81) | " | 54 |
| (46) | " | 41 | (83) | " | 42 |
| (47) | 50 | 43 | | | |

TABLE 12-2

| Compound No. | Dosage (mg/kg) | ΔPmax (mmHg) |
|---|---|---|
| Comparative compound No. 1 (Note 1) | 100 | 31 |
| Comparative compound No. 2 (Note 2) | " | 11 |
| Comparative compound No. 3 (Note 3) | " | 10 |

Note 1: isoquinoline with SO$_2$NH(CH$_2$)$_2$NH$_2$ substituent

Note 2: isoquinoline with SO$_2$N-piperazine substituent

Note 3: isoquinoline with SO$_2$N-(2-methylpiperazine) substituent

APPLICATION EXAMPLE 3

Effect of the compounds of the present invention on dilation of femoral and vertebral arteries was examined according to the method as mentioned hereinbefore. The results are shown in Table 13.

APPLICATION EXAMPLE 4

Effect of the compounds of the present invention on a "two-hemorrhage" canine model of delayed cerebral vesospasm was examined according to the method as mentioned hereinbefore. The results are shown in Table 14.

APPLICATION EXAMPLE 5

Acute toxicity test of the compounds of the present invention was effected according to the method as mentioned hereinbefore. The results are shown in Table 15.

TABLE 13

| Compound No. | Dosage (mg/kg) | Increase in femoral artery blood flow (%) | Increase in vertebral artery blood flow (%) |
|---|---|---|---|
| (1) | 0.3 | 48 | 160 |
| (3) | 0.3 | 35 | 78 |
| (18) | 0.3 | 45 | 110 |
| (83) | 0.3 | 30 | 48 |
| Comparative Compound No. 2 (Note) | 0.3 | 20 | 36 |
| | 1 | 69 | 98 |

Note:

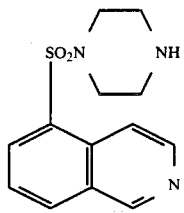

TABLE 14

| Compound No. | Dosage (mg/kg) | Increase in diameter of basilar artery (%) |
|---|---|---|
| (1) | 1 | 21 |
| | 3 | 33 |
| | 10 | 45 |
| (83) | 3 | 19 |
| | 10 | 20 |

TABLE 15

| Compound No. | LD$_{50}$ (mg/kg) |
|---|---|
| (1) | 73.5 |
| (3) | 120 |
| (18) | 197 |
| (31) | 160 |
| (54) | 135 |
| (83) | 145 |
| Comparative Compound No. 2 (Note 1) | 29 |
| Comparative Compound No. 4 (Note 2) | 48 |

Note 1:

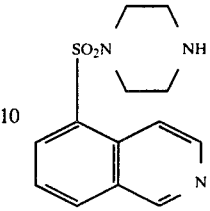

Note 2:

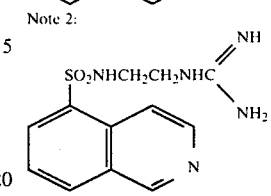

What is claimed is:

1. An isoquinolinesulfonyl compound represented by the formula (I):

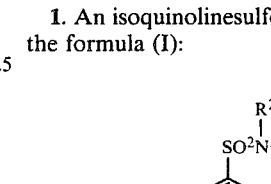 (I)

wherein $R^1$ represents a hydrogen atom, a chlorine atom or a hydroxyl group; and when $R^1$ represents a hydrogen atom, A represents an ethylene group unsubstituted or substituted with an alkyl group having 1 to 6 carbon atoms, a phenyl group or a benzyl group, $R^2$ and $R^3$ are directly bonded with each other, thereby forming a trimethylene group unsubstituted or substituted with an alkyl group having 1 to 6 carbon atoms, a phenyl group or a benzyl group, and $R^4$ represents a hydrogen atom or an alkyl group having 1 to 6 carbon atoms; and when $R^1$ represents a chlorine atom or a hydroxyl group, A represents an alkylene group having 2 to 6 carbon atoms, said group being unsubstituted or substituted with an alkyl group having 1 to 6 carbon atoms, $R^2$ and $R^3$ are not bonded with each other and each independently represent a hydrogen atom or an alkyl group having 1 to 6 carbon atoms, or $R^2$ and $R^3$ are directly bonded with each other, thereby forming an ethylene group unsubstituted or substituted with an alkyl group having 1 to 6 carbom atoms or a trimethylene group unsubstituted or substituted with an alkyl group having 1 to 6 carbon atoms, and $R^4$ represents a hydrogen atom, an alkyl group having 1 to 6 carbon atoms or an amidino group, provided that when $R^1$ represents a chlorine atom and $R^2$ and $R^3$ are directly bonded with each other thereby forming an unsubstituted trimethylene group, $R^4$ represents a hydrogen atom or an alkyl group having 1 to 6 carbon atoms;

or an acid salt thereof.

2. A compound according to claim 1, wherein $R^1$ and $R^4$ both represent a hydrogen atom.

3. A compound according to claim 2, wherein A represents an unsubstituted ethylene group, and $R^2$ and $R^3$ are directly bonded with each other, thereby forming an unsubstituted trimethylene group.

4. A compound according to claim 2, wherein A represents an ethylene group substituted with an alkyl group having 1 to 6 carbon atoms or a phenyl group, and $R^2$ and $R^3$ are directly bonded with each other, thereby forming an unsubstituted trimethylene group.

5. A compound according to claim 2, wherein A represents an unsubstituted ethylene group, and $R^2$ and $R^3$ are directly bonded with each other, thereby forming a trimethylene group substituted with an alkyl group having 1 to 6 carbon atoms or a benzyl group.

6. A compound according to claim 1, wherein $R^1$ represents a hydrogen atom; A represents an unsubstituted ethylene group; $R^2$ and $R^3$ are directly bonded with each other, thereby forming an substituted trimethylene group; and $R^4$ represents an alkyl having 1 to 6 carbon atoms.

7. A compound according to claim 1, wherein $R^1$ represents a chlorine atom or a hydroxyl group, and $R^2$ represents a hydrogen atom.

8. A compound according to claim 7, wherein $R^3$ and $R^4$ both represent a hydrogen atom, and A represents an alkylene group having 2 to 4 carbon atoms, said group being unsubstituted or substituted with a methyl group.

9. A compound according to claim 7, wherein $R^3$ and $R^4$ each independently represent a hydrogen atom or an alkyl group having 1 to 6 carbon atoms, and A represents an unsubstituted ethylene group.

10. A compound according to claim 9, wherein $R^3$ represents a hydrogen atom, and $R^4$ represents an alkyl group having 1 to 6 carbon atoms.

11. A compound according to claim 7, wherein $R^3$ represents a hydrogen atom; $R^4$ represents an amidino group; and A represents an alkylene group having 2 to 6 carbon atoms, said group being unsubstituted or substituted with an alkyl group having 1 to 6 carbon atoms.

12. A compound according to claim 1, wherein $R^1$ represents a chlorine atom or a hydroxyl group; A represents an ethylene group unsubstituted or substituted with 1 to 4 carbon atoms; $R^2$ and $R^3$ are directly bonded with each other, thereby forming an ethylene group unsubstituted or substituted with an alkyl group having 1 to 4 carbon atoms or a trimethylene group unsubstituted or substituted with an alkyl group having 1 to 4 carbon atoms; and $R^4$ represents a hydrogen atom, an alkyl group having 1 to 6 carbon atoms or an amidino group, providing that when $R^1$ represents a chlorine atom and $R^2$ and $R^3$ are directly bonded with each other thereby forming an unsubstituted trimethylene group, $R^4$ represents a hydrogen atom or an alkyl group having 1 to 6 carbon atoms.

13. A compound according to claim 12, wherein A represents an ethylene group unsubstituted or substituted with a methyl group; $R^2$ and $R^3$ are directly bonded with each other, thereby forming an ethylene group unsubstituted or substituted with an alkyl group having 1 to 4 carbon atoms; and $R^4$ represents a hydrogen atom, a methyl group or an amidino group.

14. A compound according to claim 12, wherein A represents an unsubstituted ethylene group; $R^2$ and $R^3$ are directly bonded with each other, thereby forming an unsubstituted trimethylene group; and $R^4$ represents a hydrogen atom or an amidino group.

15. A compound according to claim 14, wherein $R^1$ represents a hydroxyl group, and $R^4$ represents a hydrogen atom.

16. 1-Chloro-5-isoquinolinesulfonic acid.

17. 1-Chloro-5-isoquinolinesulfonyl chloride or an acid salt thereof.

18. A pharmaceutical composition comprising a compound of the formula (I) in claim 1 as an essential active component and a pharmaceutically acceptable non-toxic carrier.

19. A method of increasing the diameter of a human blood vessel which comprises intravenously or orally administering to human body an isoquinolinesulfonyl compound represented by the formula (I):

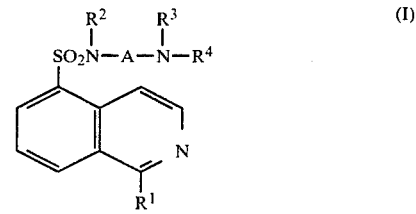

wherein $R^1$ represents a hydrogen atom, a chlorine atom or a hydroxyl group; and when $R^1$ represents a hydrogen atom, A represents an ethylene group unsubstituted or substituted with an alkyl group having 1 to 6 carbon atoms, a phenyl group or a benzyl group, $R^2$ and $R^3$ are directly bonded with each other, thereby forming a trimethylene group unsubstituted or substituted with an alkyl group having 1 to 6 carbon atoms, a phenyl group or a benzyl group, and $R^4$ represents a hydrogen atom or an alkyl group having 1 to 6 carbon atoms; and when $R^1$ represents a chlorine atom or a hydroxyl group, A represents an alkylene group having 2 to 6 carbon atoms, said group being unsubstituted or substituted with an alkyl group having 1 to 6 carbon atoms, $R^2$ and $R^3$ are not bonded with each other and each independently represent a hydrogen atom or an alkyl group having 1 to 6 carbon atoms, or $R^2$ and $R^3$ are directly bonded with each other, thereby forming an ethylene group unsubstituted or substituted with an alkyl group having 1 to 6 carbon atoms or a trimethylene group unsubstituted or substituted with an alkyl group having 1 to 6 carbon atoms, and $R^4$ represents a hydrogen atom, an alkyl group having 1 to 6 carbon atoms or an amidino group; or an acid salt thereof.

* * * * *

UNITED STATES PATENT AND TRADEMARK OFFICE
CERTIFICATE OF CORRECTION

PATENT NO. : B1 4,678,783
DATED : April 4, 1995
INVENTOR(S) : Hidaka, et al

It is certified that error appears in the above-indentified patent and that said Letters Patent is hereby corrected as shown below:

Column 2, line 14, In claim 2, line 1, change "claim 1 or 26" to -- claim 1 or 25 --.

Column 2, line 16, In claim 3, line 1, change: "[3. A compound" to -- 3. [A compound --.

Column 2, line 22. In claim 18, line 2, change "claim 1, 3, 26 or 27" to -- claim 1, 3, 25 or 26 --.

Signed and Sealed this

Ninth Day of January, 1996

Attest:

BRUCE LEHMAN

*Attesting Officer*    *Commissioner of Patents and Trademarks*

REEXAMINATION CERTIFICATE (2519th)

United States Patent [19]

Hidaka et al.

[11] B1 4,678,783

[45] Certificate Issued   Apr. 4, 1995

[54] SUBSTITUTED ISOQUINOLINESULFONYL COMPOUNDS

[75] Inventors: Hiroyoshi Hidaka, 799-75, Kannonji-Cho, Tsu-shi, Mie-ken; Takanori Sone, Nobeoka, both of Japan

[73] Assignees: Asahi Kasei Kogyo Kabushiki Kaisha, Osaka; Hiroyoshi Hidaka, Tsu, both of Japan

Reexamination Request:
No. 90/003,276, Dec. 7, 1993

Reexamination Certificate for:
Patent No.: 4,678,783
Issued: Jul. 7, 1987
Appl. No.: 813,973
Filed: Dec. 27, 1985

Related U.S. Application Data

[63] Continuation-in-part of Ser. No. 548,722, Nov. 4, 1983, Pat. No. 4,634,770.

[30] Foreign Application Priority Data

Dec. 27, 1984 [JP] Japan ................. 59-273908
Apr. 2, 1985 [JP] Japan ................. 60-68512

[51] Int. Cl.⁶ ............... A61K 31/495; A61K 31/47; C07D 401/12; C07D 217/22
[52] U.S. Cl. ............... 514/218; 514/253; 514/307; 514/309; 540/470; 540/575; 544/363; 546/139; 546/141
[58] Field of Search ........ 546/139, 141; 544/363; 540/470, 575; 514/218, 253, 307, 309

[56] References Cited
U.S. PATENT DOCUMENTS 4,097,472 6/1978 Okamoto et al. .......... 514/20
4,097,591 6/1978 Okamoto et al. .......... 514/20
4,456,757 6/1984 Hidaka et al. ............ 546/139

FOREIGN PATENT DOCUMENTS
0109023B1 5/1984 European Pat. Off. ........ 514/218

*Primary Examiner*—Alan Rotman

[57] ABSTRACT

An isoquinolinesulfonyl compound represented by the formula (I):

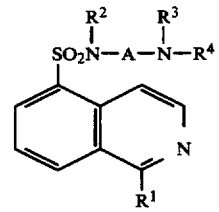

wherein
R¹: H, Cl, OH
A: unsubstituted or substituted ethylene or alkylene
R², R³: H, alkyl, jointly forming unsubstituted or substituted ethylene or trimethylene
R⁴: H, alkyl, amidino or an acid salt thereof.

They can be prepared, for example, by converting 1-R¹ substituted-5-isoquinolinesulfonic acid to the corresponding sulfonyl chloride and subsequently reacting the chloride with a compound of formula

They can be advantageously utilized as vasodilator, cerebral circulation ameliorator, antihypertensive agent and drugs for prevention and treatment of various circulatory organ diseases.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN:

Column 1, immediately following the title:

*This is a continuation-in-part of application Ser. No. 06/548,722, filed Nov. 4, 1983, now U.S. Pat. No. 4,634,770.*

AS A RESULT OF REEXAMINATION, IT HAS BEEN DETERMINED THAT

The patentability of claims 16, 17 and 19 is confirmed.

Claims 1-3, and 18 are determined to be patentable as amended.

Claims 4-15 dependent on an amended claim are determined to be patentable.

New claims 20-26 are added and determined to be patentable.

1. An isoquinolinesulfonyl compound represetned by the formula (I):

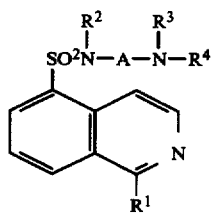

wherein R¹ represents a hydrogen atom, a chlorine atom or a hydroxyl group; and when R¹ represents a hydrogen atom,
A represents an ethylene group unsubstituted or substituted with an alkyl group having 1 to 6 carbon atoms, a phenyl group or a benzyl group,
R² and R³ are directly bonded with each other, thereby forming a trimethylene group [unsubstitued or] substituted with an alkyl group having 1 to 6 carbon atoms, a phenyl group or a benzyl group, and
R⁴ represents a hydrogen atom or an alkyl group having 1 to 6 carbon atoms; and when R¹ represents a chlorine atom or a hydroxyl group,
A represents an alkylene group having 2 to 6 carbon atoms, said group being unsubstituted or substituted with an alkyl group having 1 to 6 carbon atoms,
R² and R³ are not bonded with each other and each independently represent a hydrogen atom or an alkyl group having 1 to 6 carbon atoms, or R² and R³ are directly bonded with each other, thereby forming an ethylene group unsubstituted or substituted with an alkyl group having 1 to 6 carbon atoms or a trimethylene group unsubstituted or substituted with an alkyl group having 1 to 6 carbon atoms, and R⁴ represents a hydrogen atom, an alkyl group having 1 to 6 carbon atoms or an amidino group provided that when R¹ represents a chlorine atom and R² and R³ are directly bonded with each other thereby forming an unsubstituted trimethylene group, R⁴ represents a hydrogen atom or an alkyl group having 1 to 6 carbon atoms;

or an acid salt thereof.

2. A compound according to claim 1 *or 26* wherein R¹ and R⁴ both represent a hydrogen atom.

[3. A compound according to claim 2 wherein A represents an unsubstituted ethylene group and R³ and R³ are directly bonded with each other thereby forming an unsubstituted trimethylene group] *1-(5-isoquinolinesulfonyl)homopiperazine.*

18. A pharmaceutical composition comprising a compound of [the formula (I) in] claim 1, *3, 26 or 27* as an essential active component and a pharmaceutically acceptable non-toxic carrier.

*20. A compound according to claim 25 wherein A represents an ethylene group substituted with an phenyl group or a benzyl group.*

*21. A pharmaceutical composition comprising a compound of claim 20 as an essential active component, and a pharmaceutically acceptable carrier.*

*22. A method according to claim 19 wherein A represents an ethylene group substituted with a phenyl group or a benzyl group.*

*23. A method according to claim 19 or 22 wherein R¹ and R⁴ both represent a hydrogen atom.*

*24. A method according to claim 23 wherein A represents an unsubstituted ethylene group, and R² and R³ are directly bonded with each other, thereby forming an unsubstituted trimethylene group.*

*25. An isoquinolinesulfonyl compound represented by the formula (I) :*

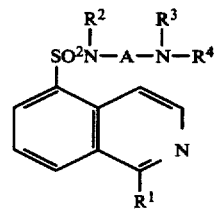

*wherein R¹ represents a hydrogen atom;*
*A represents an ethylene group substituted with an alkyl group having 1 to 6 carbon atoms, a phenyl group or a benzyl group;*
*R² and R³ are directly bonded with each other, thereby forming a trimethylene group unsubstitued or substituted with an alkyl group having 1 to 6 carbon atoms, a phenyl group or a benzyl group, and*
*R⁴ represents a hydrogen atom or an alkyl group having 1 to 6 carbon atoms.*

*26. An isoquinolinesulfonyl compound represented by the formula (I):*

(I) 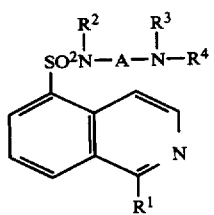

wherein $R^1$ represents a hydrogen atom;
A represents an ethylene group unsubstituted or substituted with an alkyl group having 1 to 6 carbon atoms, a phenyl group or a benzyl group;
$R^2$ and $R^3$ are directly bonded with each other, thereby forming a trimethylene group unsubstituted or substituted with an alkyl group having 1 to 6 carbon atoms, a phenyl group or a benzyl group; and
$R^4$ represents alkyl group having 1 to 6 carbon atoms.

* * * * *